United States Patent
Jandura et al.

(10) Patent No.: US 7,396,857 B2
(45) Date of Patent: *Jul. 8, 2008

(54) THERAPEUTIC COMBINATIONS FOR THE TREATMENT OR PREVENTION OF DEPRESSION

(75) Inventors: Janet Jandura, Havertown, PA (US); Sharon Rosenzweig-Lipson, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/409,480

(22) Filed: Apr. 21, 2006

(65) Prior Publication Data

US 2006/0258715 A1    Nov. 16, 2006

Related U.S. Application Data

(60) Provisional application No. 60/674,048, filed on Apr. 22, 2005.

(51) Int. Cl.
*A61K 31/34* (2006.01)
*C07D 307/00* (2006.01)

(52) U.S. Cl. ................................. 514/469; 549/467
(58) Field of Classification Search ............ 549/467; 514/469
See application file for complete search history.

(56) References Cited

U.S. PATENT DOCUMENTS

| | | | |
|---|---|---|---|
| 3,513,239 | A | 5/1970 | Wiley |
| 3,759,927 | A | 9/1973 | Huebner |
| 4,617,314 | A | 10/1986 | Tahara et al. |
| 5,756,532 | A | 5/1998 | Stack et al. |
| 6,150,402 | A | 11/2000 | Wechter et al. |
| 6,274,171 | B1 | 8/2001 | Sherman et al. |
| 6,403,120 | B1 | 6/2002 | Sherman et al. |
| 6,419,958 | B2 | 7/2002 | Sherman et al. |
| 6,444,708 | B2 | 9/2002 | Rudolph et al. |
| 6,638,972 | B2 | 10/2003 | Kelly et al. |
| 6,667,322 | B2 | 12/2003 | Gross et al. |
| 6,706,757 | B2 | 3/2004 | Greenblatt et al. |
| 6,969,730 | B2 | 11/2005 | Cowart et al. |
| 7,045,545 | B1 | 5/2006 | Briner et al. |
| 7,208,502 | B2 | 4/2007 | Solow-Cordero et al. |
| 2003/0092770 | A1 | 5/2003 | Sholnick |
| 2003/0134835 | A1 | 7/2003 | Hancock et al. |
| 2004/0029972 | A1 | 2/2004 | Howard, Jr. |
| 2005/0124692 | A1 | 6/2005 | Gross et al. |
| 2005/0143452 | A1 | 6/2005 | Gross et al. |
| 2005/0261347 | A1 | 11/2005 | Gross et al. |
| 2006/0089405 | A1 | 4/2006 | Zhou et al. |
| 2006/0111438 | A1 | 5/2006 | Gontcharov et al. |
| 2006/0241176 | A1 | 10/2006 | Stack et al. |
| 2006/0246551 | A1 | 11/2006 | Stack et al. |
| 2006/0247276 | A1 | 11/2006 | Gross et al. |
| 2006/0251172 | A1 | 11/2006 | Zhou et al. |
| 2006/0252825 | A1 | 11/2006 | Tadyson et al. |
| 2006/0258639 | A1 * | 11/2006 | Logue et al. ............ 514/211.13 |
| 2006/0258711 | A1 | 11/2006 | Rosenzweig-Lipson |
| 2006/0258712 | A1 | 11/2006 | Jacobson |
| 2006/0258713 | A1 | 11/2006 | Rosenzweig-Lipson |
| 2006/0258714 | A1 | 11/2006 | Heffernan et al. |
| 2006/0258739 | A1 * | 11/2006 | Ai et al. ..................... 514/469 |
| 2007/0032515 | A1 | 2/2007 | Anand et al. |
| 2007/0225334 | A1 | 9/2007 | Rosenzweig-Lipson |

FOREIGN PATENT DOCUMENTS

| | | |
|---|---|---|
| DE | 19909760 | 10/1999 |
| JP | 06316563 | 11/1994 |
| WO | WO-96/15099 | 5/1996 |
| WO | WO-96/15100 | 5/1996 |
| WO | WO-00/76990 | 12/2000 |
| WO | WO-2004/089410 | 10/2004 |
| WO | WO-2005/073210 A1 | 8/2005 |
| WO | WO-2005/123681 A1 | 12/2005 |
| WO | WO-2006/000902 A1 | 1/2006 |

OTHER PUBLICATIONS

Apiquian, R., et al., Amoxapine as an Atypical Antipsychotic: A Comparative Study Vs Risperidone, Neuropsychopharmacology, 30, 2236-2244 (2005).*
U.S. Appl. No. 11/787,929, Yu et al.
U.S. Appl. No. 11/787,860, Gontcharov et al.
U.S. Appl. No. 11/787,663, Mirmehrabi et al.
Di Matteo, et al., "Selective blockade of serotonin 2C/2B receptors enhances dopamine release in the rat nucleus accumbens",*Neuropharmacology*, 37: 265-272, 1998.
Office Action mailed Oct. 17, 2007 in U.S. Appl. No. 10/970,103 filed Oct. 21, 2004.
Office Action mailed Aug. 27, 2007 in U.S. Appl. No. 10/970,714 filed Oct. 21, 2004.
Office Action mailed Sep. 21, 2007 in U.S. Appl. No. 11/113,170 filed Apr. 22, 2005.

(Continued)

*Primary Examiner*—James O. Wilson
*Assistant Examiner*—Erich A Leeser
(74) *Attorney, Agent, or Firm*—Andrea L. C. Robidoux; Choate, Hall & Stewart, LLP

(57) ABSTRACT

Therapeutic combinations useful in the treatment or prevention of depression or other mood disorders, to pharmaceutical compositions containing said combinations, and to their use in the treatment or prophylaxis of depression or other mood disorders are provided. Such compounds are of formula I:

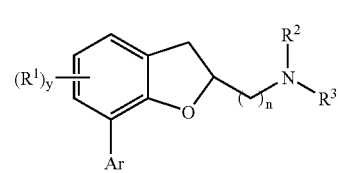

or a pharmaceutically acceptable salt thereof, wherein each of $R^1$, $R^2$, $R^3$, n, y, and Ar are as defined and described herein.

16 Claims, 1 Drawing Sheet

OTHER PUBLICATIONS

Office Action mailed Sep. 25, 2007 in U.S. Appl. No. 11/409,479 filed Apr. 21, 2006.
Office Action mailed Sep. 28, 2007 in U.S. Appl. No. 11/408,319 filed Apr. 21, 2006.
Office Action mailed Oct. 22, 2007 in U.S. Appl. No. 11/409,303 filed Apr. 21, 2006.
Office Action mailed Sep. 19, 2007 in U.S. Appl. No. 11/408,879 filed Apr. 21, 2006.
Office Action mailed Oct. 18, 2007 in U.S. Appl. No. 11/408,909 filed Apr. 21, 2006.
Notice of Allowance mailed Oct. 17, 2007 in U.S. Appl. No. 11/409,467 filed Apr. 21, 2006.
Di Matteo, et al., "SB 242 084, a selective serotonin 2C receptor antagonist, increases dopaminergic transmissions in the mesolibic system", *Neuropharmacology*, 38: 1195-1205, 1999.
International Search Report, PCT/US2006/015191.

* cited by examiner

Effect of Compound 1 (ip, 30 min pre) in the mouse tail suspension test.

Effect of Compound 1 (0.1 mg/kg ip) + paroxetine (10 or 30 mg/kg) in the mouse tail suspension test.

\* $p < 0.05$ vs. veh/veh

THERAPEUTIC COMBINATIONS FOR THE TREATMENT OR PREVENTION OF DEPRESSION

CROSS REFERENCE TO RELATED APPLICATIONS

This application claims priority to U.S. Provisional Patent Application Ser. No. 60/674,048, filed Apr. 22, 2005, the entirety of which is hereby incorporated herein by reference.

FIELD OF THE INVENTION

The present invention relates to therapeutic combinations of compounds useful for the treatment or prophylaxis of depression, to pharmaceutical compositions containing such combinations, and to their use in the treatment or prophylaxis of depression.

BACKGROUND OF THE INVENTION

Between 5-10% of adults worldwide suffer from depression. Even more experience depression-related mood disorders such as dysthymia, seasonal affective disorder, and postpartum depression, bipolar disorder, anxiety disorder, posttraumatic stress disorder, panic disorder, and obsessive-compulsive disorder.

The economic costs to society, and person costs to individuals and families, associated with depression are enormous. Within a 15-month period after having been diagnosed with depression, sufferers are four times more likely to die as those who do not have depression. Almost 60% of suicides have their roots in major depression, and 15% of those admitted to a psychiatric hospital for depression eventually kill themselves. See Nierenberg, *Am J Manag Care* 7(11 Suppl): S353-66, 2001. In the U.S. alone, the estimated economic costs for depression exceeded $44 billion in 1990. The World Health Organization estimates that major depression is the fourth most important cause worldwide of loss in disability-adjusted life years, and will be the second most important cause by 2020.

A variety of pharmacologic agents are available for the treatment of depression. Significant success has been achieved through the use of seratonin reuptake inhibitors (SRIs), norepinephrine reuptake inhibitors (NERIs), combined serotonin-norepinephrine reuptake inhibitors (SNRIs), monoamine oxidase inhibitors (MAOIs), phosphodiesterase-4 (PDE4) inhibitors or other compounds. However, even with these options available, many patients fail to respond, or respond only partially to treatment. Additionally, many of these agents show delayed onset of activity, so that patients are required to undergo treatment for weeks or months before receiving benefits. Most currently available antidepressants take 2-3 weeks or more to elicit a response.

Traditional therapies can also have significant side effects. For example, more than a third of patients taking SRIs experience sexual dysfunction. Other problematic side effects include gastrointestinal disturbances, often manifested as nausea and occasional vomiting, agitation, insomnia, weight gain, onset of diabetes, prolongation of the heart rate corrected interval (QTc), agranylocytosis, etc. Depressive patients who also suffer from psychotic disorders (e.g., schizophrenia) also sometimes suffer extrapyramidal side effects. These side effects often discourage patients from following their recommended therapeutic regimen.

There remains a need for the development of improved therapies for the treatment of depression and/or other mood disorders.

SUMMARY OF THE INVENTION

The present invention provides new combination therapies for the treatment of depression. In particular, the present invention provides combinations of a compound of formula I:

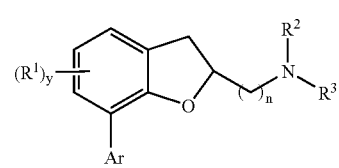

or a pharmaceutically acceptable salt thereof, wherein:

n is one or two;

each of $R^2$ and $R^3$ is independently hydrogen, methyl, ethyl, 2-fluoroethyl, 2,2-difluoroethyl or cyclopropyl;

each $R^1$ is independently hydrogen, halogen, OH, lower alkyl, lower alkoxy, lower haloalkyl, lower haloalkoxy, or CN;

Ar is thienyl, furyl, pyridyl, or phenyl, wherein Ar is optionally substituted with one or more $R^x$ substituents;

each $R^x$ is independently selected from halogen, OH, lower alkyl, lower alkoxy, lower haloalkyl, lower haloalkoxy, or CN; and y is 0-3, with one or more anti-depressive agents for treating patients suffering from or susceptible to depression or related mood disorders. The present invention therefore provides, among other things, certain drug combinations, pharmaceutical compositions containing such combinations, and methods of treating patients suffering from or susceptible to depression or related mood disorders with such combinations or compositions.

DETAILED DESCRIPTION OF CERTAIN EMBODIMENTS OF THE INVENTION

Figure 1:
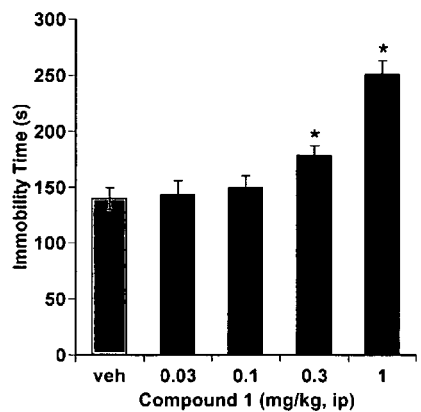
FIG. 1 shows the effects of Compound 1, alone or in combination with paroxetine, in the tail suspension test.
Figure 1:
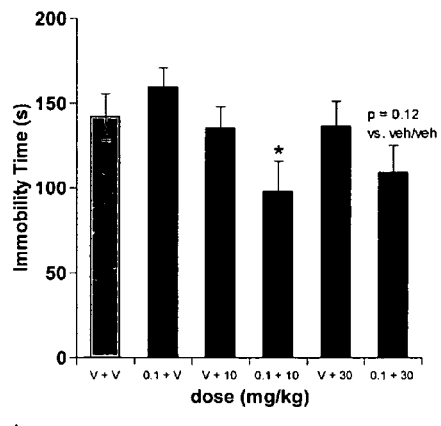

The present invention encompasses the finding that certain 5-$HT_{2C}$ receptor agonists can be usefully combined with one or more anti-depressive agents in the treatment or prevention of depression or other mood disorders. In particular, the present invention provides combinations of 5-$HT_{2C}$ receptor agonists, or partial agonists, of formula I:

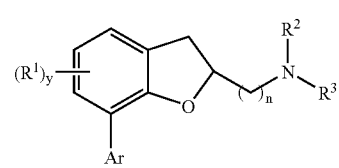

or a pharmaceutically acceptable salt thereof, wherein:

n is one or two;

each of $R^2$ and $R^3$ is independently hydrogen, methyl, ethyl, 2-fluoroethyl, 2,2-difluoroethyl or cyclopropyl;

each R¹ is independently hydrogen, halogen, OH, lower alkyl, lower alkoxy, lower haloalkyl, lower haloalkoxy, or CN;

Ar is thienyl, furyl, pyridyl, or phenyl, wherein Ar is optionally substituted with one or more R^x substituents;

each R^x is independently selected from halogen, OH, lower alkyl, lower alkoxy, lower haloalkyl, lower haloalkoxy, or CN; and y is 0-3, with one or more anti-depressant drugs for the treatment of depression or other mood disorders. In some embodiments, the inventive combinations allow treatment of refractory depression (i.e., depression that is not responsive to traditional therapies). Alternatively or additionally, the inventive combinations may be employed to treat depression with more rapid onset of benefit, and/or with fewer side effects.

1. 5-HT$_{2C}$ Receptor Agonists of Formula I

The present invention utilizes 5-HT$_{2C}$ receptor agonists of formula I:

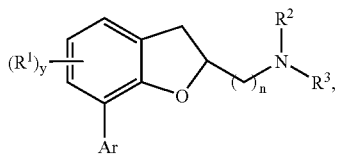

wherein:

n is one or two;

each of R² and R³ is independently hydrogen, methyl, ethyl, 2-fluoroethyl, 2,2-difluoroethyl or cyclopropyl;

each R¹ is independently hydrogen, halogen, OH, lower alkyl, lower alkoxy, lower haloalkyl, lower haloalkoxy, or CN;

Ar is thienyl, furyl, pyridyl, or phenyl, wherein Ar is optionally substituted with one or more Rx substituents;

each R^x is independently selected from halogen, OH, lower alkyl, lower alkoxy, lower haloalkyl, lower haloalkoxy, or CN; and y is 0-3, or pharmaceutically acceptable salts thereof, in combination with one or more anti-depressants.

The term "lower alkyl," as used herein, refers to a hydrocarbon chain having up to 4 carbon atoms, preferably 1 to 3 carbon atoms, and more preferably 1 to 2 carbon atoms. The term "alkyl" includes, but is not limited to, straight and branched chains such as methyl, ethyl, n-propyl, isopropyl, n-butyl, isobutyl, sec-butyl, or t-butyl.

The term "alkoxy," as used herein, refers to the group —OR, wherein R is a lower alkyl group.

The terms "halogen" or "halo," as used herein, refer to chlorine, bromine, fluorine or iodine.

The term "haloalkyl," as used herein, or as part of a moiety such as "haloalkoxy" refers to an alkyl group, as defined herein, that has one or more halogen substituents. In certain embodiment, every hydrogen atom on said alkyl group is replaced by a halogen atom. Such haloalkyl groups include —CF$_3$. Such haloalkoxy groups include —OCF$_3$.

The terms "effective amount" and "therapeutically effective amount," as used herein, refer to the amount of a compound or combination that, when administered to an individual, is effective to treat, prevent, delay, or reduce the severity of depression or another mood disorder from which the individual suffers or to which the individual is susceptible, or from one or more symptoms of depression or other mood disorder. Those of ordinary skill in the art will appreciate that the amount of an individual active agent that is therapeutically effective in the context of an inventive combination may well differ from the amount of that agent that is therapeutically effective when the agent is delivered alone. In some embodiments of the invention, a lower amount is required to therapeutic effectiveness in the context of an inventive combination than is required to achieve therapeutic effectiveness alone. Those of ordinary skill will further appreciate that a different amount of a particular compound or combination may be required to achieve therapeutic effectiveness in the context of different formulations, modes of delivery and/or administration regimen.

The term "pharmaceutically acceptable salts" or "pharmaceutically acceptable salt" refers to salts derived from treating a compound of formula I with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids. In certain embodiments, the present invention provides the hydrochloride salt of a compound of formula I.

The term "patient," as used herein, refers to a mammal. In certain embodiments, the term "patient" refers to a human.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The compounds of formula I, as defined above or in classes and subclasses as described herein, have affinity for and agonist or partial agonist activity at the 2C subtype of brain serotonin receptors.

As defined generally above, each of the R² and R³ groups of formula I is independently hydrogen, methyl, ethyl, 2-fluoroethyl, 2,2-difluoroethyl or cyclopropyl. In certain embodiments, one of the R² and R³ groups of formula I is hydrogen and the other R² or R³ group of formula I is hydrogen, methyl, ethyl, 2-fluoroethyl, 2,2-difluoroethyl or cyclopropyl. In other embodiments, neither of the R² and R³ groups of formula I is hydrogen. In still other embodiments, both of the R² and R³ groups of formula I are hydrogen.

As defined generally above, each R¹ group of formula I is independently hydrogen, halogen, OH, lower alkyl, lower alkoxy, lower haloalkyl, lower haloalkoxy, or CN. In certain embodiments, each R¹ group of formula I is hydrogen. In other embodiments, at least one of R¹ group of formula I is halogen. In still other embodiments, y is 1 and R¹ is halogen.

According to another embodiment, y is 1 and R¹ is at the 5-position of the dihydrobenzofuran ring of formula I, thus forming a compound of formula Ia:

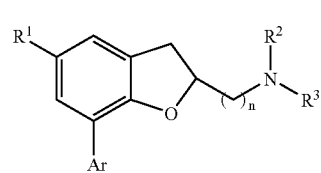

or a pharmaceutically acceptable salt thereof, wherein each of R, $R^2$, $R^3$, Ar, and n are as defined above for compounds of formula I and in classes and subclasses as described above and herein.

According to yet another embodiment, y is 1 and $R^1$ is at the 6-position of the dihydrobenzofuran ring of formula I, thus forming a compound of formula Ia':

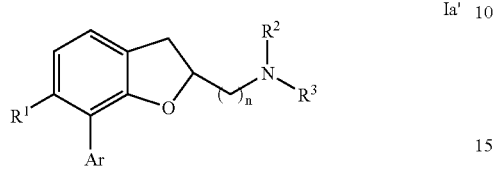

Ia' or a pharmaceutically acceptable salt thereof, wherein each of $R^1$, $R^2$, $R^3$, Ar, and n are as defined above for compounds of formula I and in classes and subclasses as described above and herein.

As defined generally above, the Ar group of formula I is thienyl, furyl, pyridyl, or phenyl, wherein Ar is optionally substituted with one or more substituents independently selected from halogen, OH, lower alkyl, lower alkoxy, haloalkyl, haloalkoxy, or CN. In certain embodiments, the Ar group of formula I is unsubstituted phenyl. In other embodiments, the Ar group of formula I is phenyl with at least one substituent in the ortho position. In other embodiments, the Ar group of formula I is phenyl with at least one substituent in the ortho position selected from halogen, lower alkyl, lower alkoxy, or trifluoromethyl. According to another aspect the present invention provides a compound of formula I wherein Ar is phenyl di-substituted in the ortho and meta positions with independently selected halogen lower alkyl, or lower alkoxy. Yet another aspect of the present invention provides a compound of formula I wherein Ar is phenyl di-subsituted in the ortho and para positions with independently selected halogen lower alkyl, or lower alkoxy. In other embodiment, the present invention provides a compound of formula I wherein Ar is phenyl di-subsituted in the ortho positions with independently selected halogen lower alkyl, or lower alkoxy. Exemplary substituents on the phenyl moiety of the Ar group of formula I include OMe, fluoro, chloro, methyl, and trifluoromethyl.

In certain embodiments, the present invention provides combinations including a compound of formula Ia' wherein Ar is phenyl with one substituent in the ortho position selected from halogen, lower alkyl, lower alkoxy, or trifluoromethyl.

According to one embodiment, Ar is phenyl substituted with one $R^x$ substituent in the ortho-position, thus forming a compound of formula Ib, or with an $R^x$ substituent in both ortho-positions, thus forming a compound of formula Ic:

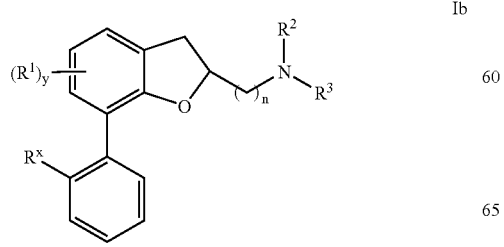

Ib

-continued

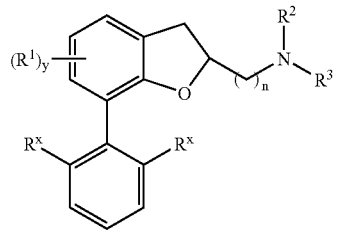

Ic or a pharmaceutically acceptable salt thereof, wherein each $R^1$, $R^2$, $R^3$, $R^x$, y and n are as defined above for compounds of formula I and in classes and subclasses as described above and herein.

In certain embodiments, the Ar group of formula I is selected from the following:

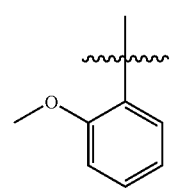

i

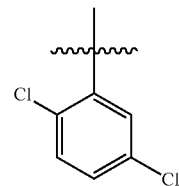

ii

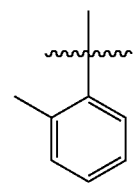

iii

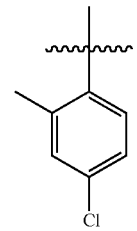

iv

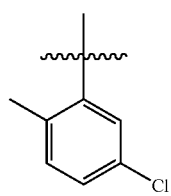

v

-continued

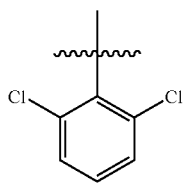
vi

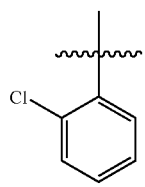
vii

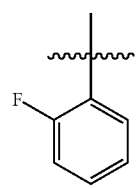
viii

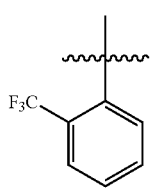
ix

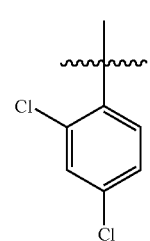
x

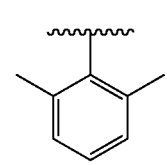
xi

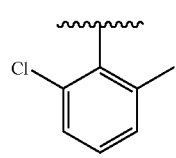
xii

-continued

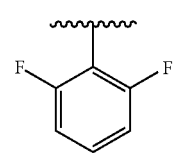
xiii

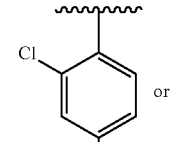 or
xiv

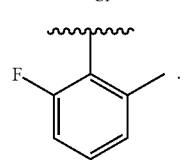 .
xv

According to yet another embodiment, the present invention provides combinations including a compound of formula Id or Ie:

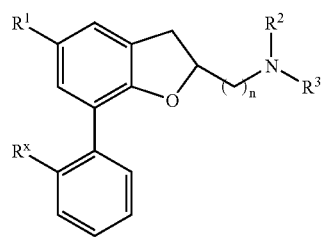
Id

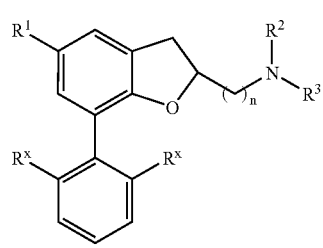
Ie or a pharmaceutically acceptable salt thereof, wherein each $R^1$, $R^2$, $R^3$, $R^x$, y and n are as defined above for compounds of formula I and in classes and subclasses as described above and herein.

According to another embodiment, the present invention provides combinations including a compound of formula If or Ig:

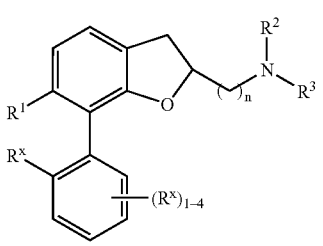
(If)

-continued

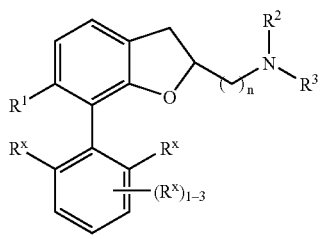
(Ig)

or a pharmaceutically acceptable salt thereof, wherein each $R^1$, $R^2$, $R^3$, $R^x$, and n are as defined above for compounds of formula I and in classes and subclasses as described above and herein.

In certain embodiments, the present invention provides a compound of formula Ih or Ii:

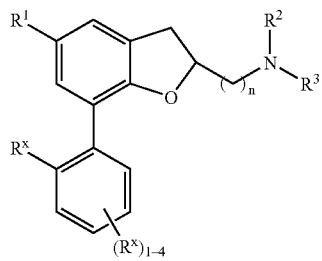
Ih

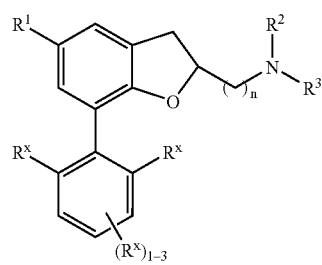
Ii or a pharmaceutically acceptable salt thereof, wherein each $R^1$, $R^2$, $R^3$, $R^x$, and n are as defined above for compounds of formula I and in classes and subclasses as described above and herein.

In certain embodiments, the present invention provides combinations including a compound of formula VIa or VIb:

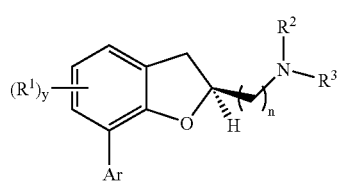
VIa

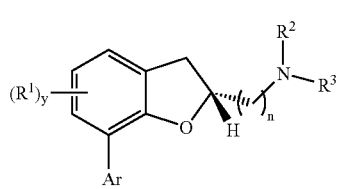
VIb or a pharmaceutically acceptable salt thereof, wherein each $R^1$, $R^2$, $R^3$, $R^x$, y and n are as defined above for compounds of formula I and in classes and subclasses as described above and herein.

According to another embodiment, the present invention provides a compound of formula VIc or VId:

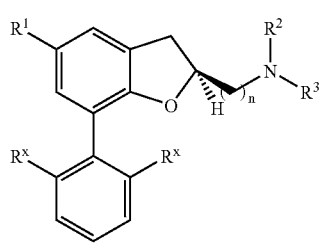
VIa

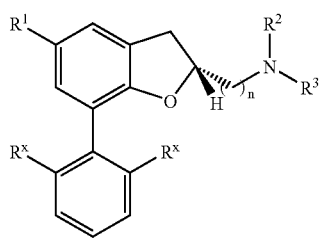
VIb or a pharmaceutically acceptable salt thereof, wherein each $R^1$, $R^2$, $R^3$, $R^x$, y and n are as defined above for compounds of formula I and in classes and subclasses as described above and herein.

Compounds of formula I for use in accordance with the present invention contain asymmetric carbon atoms and thus give rise to stereoisomers, including enantiomers and diastereomers. Accordingly, it is contemplated that the present invention relates to all of these stereoisomers, as well as to mixtures of the stereoisomers. Throughout this application, the name of a compound utilized in this invention, where the absolute configuration of an asymmetric center is not indicated, is intended to embrace the individual stereoisomers as well as mixtures of stereoisomers. In certain embodiments of the invention, compounds having an absolute (R) configuration are preferred.

Where a particular enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In certain embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, et al., *Tetrahedron* 33:2725 (1977); Eliel, *Stereochemistry of Carbon Compounds* (McGraw-Hill, NY, 1962);

Wilen, *Tables of Resolving Agents and Optical Resolutions* p. 268 (E. L. Eliel, Ed., Univ. of Notre Dame Press, Notre Dame, Ind. 1972).

It is further recognized that atropisomers of the present compounds may exist. The present invention thus encompasses atropisomeric forms of compounds of formula I as defined above, and in classes and sublcasses described above and herein.

Also, it will be appreciated by those of ordinary skill in the art that reference to a compound herein is intended to include reference to any and all related forms such as polymorphs, hydrates, etc. Also, compounds may be provided as pro-drugs or other forms converted into the active agent during manufacture, processing, formulation, delivery, or in the body.

It will additionally be appreciated that the principles of the present invention apply all radiolabelled forms of the compounds receited herein, including, for example, those where the radiolabels are selected from as $^{3}$H, $^{11}$C, $^{14}$C, $^{18}$F, $^{123}$I and $^{125}$I. Such radiolabelled compounds are useful as research and diagnostic tools in metabolism pharmacokinetics studies and in binding assays in both animals and humans.

Exemplary compounds for formula I useful for the practice of the present invention are set forth in Table 1, below.

TABLE 1

Exemplary Compounds of Formula I (±)-1-{7-[3,5-bis(trifluoromethyl)phenyl]-2,3-dihydro-1-benzofuran-2-yl}methanamine,
(±)-1-[7-(3-chloro-4-fluorophenyl)-2,3-dihydro-1-benzofuran-2-yl]methanamine,
(±)-1-[7-(3,5-dichlorophenyl)-2,3-dihydro-1-benzofuran-2-yl]methanamine,
(±)-1-(7-phenyl-2,3-dihydro-1-benzofuran-2-yl)methanamine,
(+)-(1-(7-phenyl-2,3-dihydro-1-benzofuran-2-yl)methanamine,
(−)-1-(7-phenyl-2,3-dihydro-1-benzofuran-2-yl)methanamine,
(±)-1-[7-(3-methylphenyl)-2,3-dihydro-1-benzofuran-2-yl]methanamine,
(+)-1-[7-(3-methylphenyl)-2,3-dihydro-1-benzofuran-2-yl]methanamine,
(−)-1-[7-(3-methylphenyl)-2,3-dihydro-1-benzofuran-2-yl]methanamine,
(±)-1-(7-thien-3-yl-2,3-dihydro-1-benzofuran-2-yl)methanamine,
(+)-1-(7-thien-3-yl-2,3-dihydro-1-benzofuran-2-yl)methanamine,
(−)-1-(7-thien-3-yl-2,3-dihydro-1-benzofuran-2-yl)methanamine,
(±)-1-[7-(2-methylphenyl)-2,3-dihydro-1-benzofuran-2-yl]methanamine,
(+)-1-[7-(2-methylphenyl)-2,3-dihydro-1-benzofuran-2-yl]methanamine,
(−)-1-[7-(2-methylphenyl)-2,3-dihydro-1-benzofuran-2-yl]methanamine,
(±)-1-[7-(2-fluorophenyl)-2,3-dihydro-1-benzofuran-2-yl]methanamine,
(+)-1-[7-(2-fluorophenyl)-2,3-dihydro-1-benzofuran-2-yl]methanamine,
(−)-1-[7-(2-fluorophenyl)-2,3-dihydro-1-benzofuran-2-yl]methanamine,
(±)-1-{7-[2-(trifluoromethyl)phenyl]-2,3-dihydro-1-benzofuran-2-yl}methanamine,
(−)-1-{7-[2-(trifluoromethyl)phenyl]-2,3-dihydro-1-benzofuran-2-yl}methanamine,
(+)-1-{7-[2-(trifluoromethyl)phenyl]-2,3-dihydro-1-benzofuran-2-yl}methanamine,
(±)-1-[7-(2,6-dimethylphenyl)-2,3-dihydro-1-benzofuran-2-yl]methanamine,
(−)-1-[7-(2,6-dimethylphenyl)-2,3-dihydro-1-benzofuran-2-yl]methanamine,
(+)-1-[7-(2,6-dimethylphenyl)-2,3-dihydro-1-benzofuran-2-yl]methanamine,
(±)-1-[7-(2-methoxyphenyl)-2,3-dihydro-1-benzofuran-2-yl]methanamine,
(±)-1-[7-(2-chlorophenyl)-2,3-dihydro-1-benzofuran-2-yl]methanamine,
(±)-1-[7-(3-fluorophenyl)-2,3-dihydro-1-benzofuran-2-yl]methanamine,
(±)-1-[7-(3-chlorophenyl)-2,3-dihydro-1-benzofuran-2-yl]methanamine,
(+)-1-[7-(3-chlorophenyl)-2,3-dihydro-1-benzofuran-2-yl]methanamine,
(−)-1-[7-(3-chlorophenyl)-2,3-dihydro-1-benzofuran-2-yl]methanamine,
(±)-1-[7-(3-methoxyphenyl)-2,3-dihydro-1-benzofuran-2-yl]methanamine,
(±)-1-{7-[3-(trifluoromethyl)phenyl]-2,3-dihydro-1-benzofuran-2-yl}methanamine,
(±)-1-[7-(4-methylphenyl)-2,3-dihydro-1-benzofuran-2-yl]methanamine,
(+)-1-[7-(4-methylphenyl)-2,3-dihydro-1-benzofuran-2-yl]methanamine,
(−)-1-[7-(4-methylphenyl)-2,3-dihydro-1-benzofuran-2-yl]methanamine,
(±)-1-[7-(4-fluorophenyl)-2,3-dihydro-1-benzofuran-2-yl]methanamine,
(+)-1-[7-(4-fluorophenyl)-2,3-dihydro-1-benzofuran-2-yl]methanamine,
(−)-1-[7-(4-fluorophenyl)-2,3-dihydro-1-benzofuran-2-yl]methanamine,
(±)-1-[7-(4-chlorophenyl)-2,3-dihydro-1-benzofuran-2-yl]methanamine,
(+)-1-[7-(4-chlorophenyl)-2,3-dihydro-1-benzofuran-2-yl]methanamine,
(−)-1-[7-(4-chlorophenyl)-2,3-dihydro-1-benzofuran-2-yl]methanamine,
(±)-1-[7-(4-methoxyphenyl)-2,3-dihydro-1-benzofuran-2-yl]methanamine,
(+)-1-[7-(4-methoxyphenyl)-2,3-dihydro-1-benzofuran-2-yl]methanamine,
(−)-1-[7-(4-methoxyphenyl)-2,3-dihydro-1-benzofuran-2-yl]methanamine,
(±)-1-{7-[4-(trifluoromethyl)phenyl]-2,3-dihydro-1-benzofuran-2-yl}methanamine,
(±)-1-[7-(2,4-dichlorophenyl)-2,3-dihydro-1-benzofuran-2-yl]methanamine,
(±)-1-(5-chloro-7-phenyl-2,3-dihydro-1-benzofuran-2-yl)methanamine,
(+)-1-(5-chloro-7-phenyl-2,3-dihydro-1-benzofuran-2-yl)methanamine,
(−)-1-(5-chloro-7-phenyl-2,3-dihydro-1-benzofuran-2-yl)methanamine,
(±)-1-[5-chloro-7-(2-chlorophenyl)-2,3-dihydro-1-benzofuran-2-yl]methanamine,
(±)-1-[5-chloro-7-(3-methylphenyl)-2,3-dihydro-1-benzofuran-2-yl]methanamine,
(±)-1-[5-chloro-7-(3-chlorophenyl)-2,3-dihydro-1-benzofuran-2-yl]methanamine,
(±)-(5-chloro-7-thien-3-yl-2,3-dihydro-1-benzofuran-2-yl)methylamine,
(−)-(5-chloro-7-thien-3-yl-2,3-dihydro-1-benzofuran-2-yl)methylamine,
(+)-(5-chloro-7-thien-3-yl-2,3-dihydro-1-benzofuran-2-yl)methylamine,
(+)-N-[(5-chloro-7-thien-3-yl-2,3-dihydro-1-benzofuran-2-yl)methyl]-N-methylamine,
(−)-N-[(5-chloro-7-thien-3-yl-2,3-dihydro-1-benzofuran-2-yl)methyl]-N-methylamine,
(±)-1-[5-chloro-7-(2-methylphenyl)-2,3-dihydro-1-benzofuran-2-yl]methanamine,
(+)-1-[5-chloro-7-(2-methylphenyl)-2,3-dihydro-1-benzofuran-2-yl]methanamine,
(−)-1-[5-chloro-7-(2-methylphenyl)-2,3-dihydro-1-benzofuran-2-yl]methanamine,
(±)-1-(4-fluoro-7-phenyl-2,3-dihydro-1-benzofuran-2-yl)methanamine, TABLE 1-continued Exemplary Compounds of Formula I (±)-1-[4-fluoro-7-(2-methylphenyl)-2,3-dihydro-1-benzofuran-2-yl]methanamine,
(±)-1-[7-(2-chlorophenyl)-5-fluoro-2,3-dihydro-1-benzofuran-2-yl]methanamine,
(+)-1-[7-(2-chlorophenyl)-5-fluoro-2,3-dihydro-1-benzofuran-2-yl]methanamine,
(−)-1-[7-(2-chlorophenyl)-5-fluoro-2,3-dihydro-1-benzofuran-2-yl]methanamine,
(±)-1-(5-fluoro-7-phenyl-2,3-dihydro-1-benzofuran-2-yl)methanamine,
(±)-1-[5-fluoro-7-(2-methylphenyl)-2,3-dihydro-1-benzofuran-2-yl]methanamine,
(+)-1-[5-fluoro-7-(2-methylphenyl)-2,3-dihydro-1-benzofuran-2-yl]methanamine,
(−)-1-[5-fluoro-7-(2-methylphenyl)-2,3-dihydro-1-benzofuran-2-yl]methanamine,
(±)-1-[5-fluoro-7-(2-fluorophenyl)-2,3-dihydro-1-benzofuran-2-yl]methanamine,
(±)-1-{5-fluoro-7-[2-(trifluoromethyl)phenyl]-2,3-dihydro-1-benzofuran-2-yl}methanamine,
(±)-(4,5-difluoro-7-phenyl-2,3-dihydro-1-benzofuran-2-yl)methylamine,
(±)-1-[4,5-difluoro-7-(2-methylphenyl)-2,3-dihydro-1-benzofuran-2-yl]methanamine,
(±)-1-(5-chloro-2-methyl-7-phenyl-2,3-dihydro-1-benzofuran-2-yl)methanamine,
(±)-(5-chloro-2-methyl-7-thien-3-yl-2,3-dihydro-1-benzofuran-2-yl)methylamine,
(±)-(5-chloro-2-methyl-7-thien-2-yl-2,3-dihydro-1-benzofuran-2-yl)methylamine,
(+)-1-[7-(2-methoxyphenyl)-2,3-dihydro-1-benzofuran-2-yl]methanamine,
(−)-1-[7-(2-chlorophenyl)-2,3-dihydro-1-benzofuran-2-yl]methanamine,
(+)-1-[7-(2-chlorophenyl)-2,3-dihydro-1-benzofuran-2-yl]methanamine,
(+)-1-[7-(3-fluorophenyl)-2,3-dihydro-1-benzofuran-2-yl]methanamine,
(−)-1-[7-(3-fluorophenyl)-2,3-dihydro-1-benzofuran-2-yl]methanamine,
(+)-1-[7-(3-methoxyphenyl)-2,3-dihydro-1-benzofuran-2-yl]methanamine,
(−)-1-[7-(3-methoxyphenyl)-2,3-dihydro-1-benzofuran-2-yl]methanamine,
(−)-1-{7-[3-(trifluoromethyl)phenyl]-2,3-dihydro-1-benzofuran-2-yl}methanamine,
(+)-1-{7-[3-(trifluoromethyl)phenyl]-2,3-dihydro-1-benzofuran-2-yl}methanamine,
(+)-1-{7-[4-(trifluoromethyl)phenyl]-2,3-dihydro-1-benzofuran-2-yl}methanamine,
(−)-1-{7-[4-(trifluoromethyl)phenyl]-2,3-dihydro-1-benzofuran-2-yl}methanamine,
(±)-1-[7-(2,6-difluorophenyl)-2,3-dihydro-1-benzofuran-2-yl]methanamine,
(±)-1-[7-(2,6-dichlorophenyl)-2,3-dihydro-1-benzofuran-2-yl]methanamine,
(−)-1-[7-(2,6-dichlorophenyl)-2,3-dihydro-1-benzofuran-2-yl]methanamine,
(+)-1-[7-(2,6-dichlorophenyl)-2,3-dihydro-1-benzofuran-2-yl]methanamine,
(±)-1-[7-(2,4-dimethoxyphenyl)-2,3-dihydro-1-benzofuran-2-yl]methanamine,
(−)-1-[7-(2,4-dimethoxyphenyl)-2,3-dihydro-1-benzofuran-2-yl]methanamine,
(+)-1-[7-(2,4-dimethoxyphenyl)-2,3-dihydro-1-benzofuran-2-yl]methanamine,
(±)-1-[7-(2,4-difluorophenyl)-2,3-dihydro-1-benzofuran-2-yl]methanamine,
(+)-1-[7-(2,4-difluorophenyl)-2,3-dihydro-1-benzofuran-2-yl]methanamine,
(−)-1-[7-(2,4-difluorophenyl)-2,3-dihydro-1-benzofuran-2-yl]methanamine,
(−)-1-[7-(2,4-dichlorophenyl)-2,3-dihydro-1-benzofuran-2-yl]methanamine,
(+)-1-[7-(2,4-dichlorophenyl)-2,3-dihydro-1-benzofuran-2-yl]methanamine,
(−)-1-{5-fluoro-7-[2-(trifluoromethyl)phenyl]-2,3-dihydro-1-benzofuran-2-yl}methanamine,
(+)-1-{5-fluoro-7-[2-(trifluoromethyl)phenyl]-2,3-dihydro-1-benzofuran-2-yl}methanamine,
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl)amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl)amine,
(−)-{[7-(4-chloro-2-methylphenyl)-2,3-dihydro-1-benzofuran-2-yl]methyl)amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran--yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(−)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[5-fluoro-7-(3-fluorophenyl)-2,3-dihydro-1-benzofuran-2-yl]methyl}amine,
(±)-{[5-fluoro-7-(3-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine,
(±)-{[5-fluoro-7-(4-chlorophenyl)-2,3-dihydro-1-benzofuran-2-yl]methyl}amine,
(±)-{[5-fluoro-7-(4-methylphenyl)-2,3-dihydro-1-benzofuran-2-yl]methyl}amine,
(±)-{[5-fluoro-7-(4-methoxyphenyl)-2,3-dihydro-1-benzofuran-2-yl]methyl}amine,
(±)-[(5-fluoro-7-thien-3-yl-2,3-dihydro-1-benzofuran-2-yl)methyl]amine,
(±)-{[5-fluoro-7-(3-furyl)-2,3-dihydro-1-benzofuran-2-yl]methyl}amine,
(±)-[(5-fluoro-7-pyridin-2-yl-2,3-dihydro-1-benzofuran-2-yl)methyl]amine,
(±)-[(5-fluoro-7-pyridin-3-yl-2,3-dihydro-1-benzofuran-2-yl)methyl]amine,
(−)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-[(5-fluoro-7-pyridin-4-yl-2,3-dihydro-1-benzofuran-2-yl)methyl]amine,
(±)-[(5-fluoro-7-pyrimidin-5-yl-2,3-dihydro-1-benzofuran-2-yl)methyl]amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine, TABLE 1-continued Exemplary Compounds of Formula I (−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(+)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}ethanamine,
(±)-{[7-(2,6-dichlorophenyl)-5-fluoro-2,3-dihydro-1-benzofuran-2-yl]methyl}dimethylamine,
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(3-furyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{[5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(5-chloro-2-methoxyphenyl)-2,3-dihydro-1-benzofuran-2-yl]methyl}amine,
(±)-{[5-chloro-7-(3,4-difluorophenyl)-2,3-dihydro-1-benzofuran-2-yl]methyl}amine,
(±)-{[5-chloro-7-(3-chloro-4-fluorophenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine,
(−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(+)-{[5-chloro-7-(2,6-dichlorophenyl)-2,3-dihydro-1-benzofuran-2-yl]methyl}amine,
(−)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-{[5-chloro-7-(2,6-dimethylphenyl)-2,3-dihydro-1-benzofuran-2-yl]methyl}ethanamine,
(±)-{[(5-methyl-7-phenyl-2,3-dihydro-1-benzofuran-2-yl)methyl]amine,
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine, TABLE 1-continued Exemplary Compounds of Formula I (±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±)-{[5-(trifluoromethyl)-7-(3-methylphenyl)-2,3-dihydro-1-benzofuran-2-yl]methyl}amine,
(±)-{[5-(trifluoromethyl)-7-(3-fluorophenyl)-2,3-dihydro-1-benzofuran-2-yl]methyl}amine,
(±)-{[5-(trifluoromethyl)-7-(3-chlorophenyl)-2,3-dihydro-1-benzofuran-2-yl]methyl}amine,
(±)-{[5-(trifluoromethyl)-7-(3-methoxyphenyl)-2,3-dihydro-1-benzofuran-2-yl]methyl}amine,
(±)-{[5-(trifluoromethyl)-7-(3-(trifluoromethyl)phenyl)-2,3-dihydro-1-benzofuran-2-yl]methyl}amine,
(±)-{[5-(trifluoromethyl)-7-(4-methylphenyl)-2,3-dihydro-1-benzofuran-2-yl]methyl}amine,
(±)-{[5-(trifluoromethyl)-7-(4-fluorophenyl)-2,3-dihydro-1-benzofuran-2-yl]methyl}amine,
(±)-{[5-(trifluoromethyl)-7-(4-chlorophenyl)-2,3-dihydro-1-benzofuran-2-yl]methyl}amine,
(±)-{[5-(trifluoromethyl)-7-(4-methoxyphenyl)-2,3-dihydro-1-benzofuran-2-yl]methyl}amine,
(±)-{[5-(trifluoromethyl)-7-(4-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(3,4-difluorophenyl)-5-(trifluoromethyl)-2,3-dihydro-1-benzofuran-2-yl]methyl}amine,
(±)-{[7-(3-chloro-4-fluorophenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-4-[2-(aminomethyl)-5-(trifluoromethyl)-2,3-dihydro-1-benzofuran-7-yl]benzonitrile
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[5-methoxy-7-(3-thienyl)-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxylphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl-1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine, TABLE 1-continued Exemplary Compounds of Formula I (+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[5-chloro-7-(3,4-difluorophenyl)-2,3-dihydro-1-benzofuran-2-yl]methyl}methylamine,
(±)-[5-chloro-7-(3-chloro-4-fluorophenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-N-methyl-1-[7-(2,3-difluorophenyl)-5-(trifluoromethyl)-2,3-dihydro-1-benzofuran-2-yl]methanamine,
(±)-N-methyl-1-[7-(3,4-difluorophenyl)-5-(trifluoromethyl)-2,3-dihydro-1-benzofuran-2-yl]methanamine,
(±)-N-methyl-1-[7-(2,5-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-{[7-(3-chloro-4-fluorophenyl)-5-(trifluoromethyl)-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine,
(+){[7-(2,6-dichlorophenyl)-5-fluoro-2,3-dihydro-1-benzofuran-2-yl]methyl}methylamine,
(−){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{2-[6-chloro-7-(2-chlorophenyl)-2,3-dihydro-1-benzofuran-2-yl]ethyl}amine, TABLE 1-continued Exemplary Compounds of Formula I (±)-{2-[7-(2,6-dichlorophenyl)-5-fluoro-2,3-dihydro-1-benzofuran-2-yl]ethyl}amine,
(±)-{2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{N-methyl-1-[(7-(2,4,6-trichlorophenyl)-2,3-dihydro-1-benzofuran-2-yl]methanamine,
(−)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(±)-{[7-(2,3-dimethoxyphenyl)-5-fluoro-2,3-dihydro-1-benzofuran-2-yl]methyl}methylamine;
or a pharmaceutically acceptable salt thereof.

In certain embodiments, exemplary compounds of formula I are as set forth in Table 1-a, below.

TABLE 1-a

Exemplary Compounds of formula I:

(±)-1-(7-phenyl-2,3-dihydro-1-benzofuran-2-yl)methanamine,
(+)-(1-(7-phenyl-2,3-dihydro-1-benzofuran-2-yl)methanamine,
(−)-1-(7-phenyl-2,3-dihydro-1-benzofuran-2-yl)methanamine,
(±)-1-[7-(2-methylphenyl)-2,3-dihydro-1-benzofuran-2-yl]methanamine,
(+)-1-[7-(2-methylphenyl)-2,3-dihydro-1-benzofuran-2-yl]methanamine,
(−)-1-[7-(2-methylphenyl)-2,3-dihydro-1-benzofuran-2-yl]methanamine,
(±)-1-[7-(2-fluorophenyl)-2,3-dihydro-1-benzofuran-2-yl]methanamine,
(+)-1-[7-(2-fluorophenyl)-2,3-dihydro-1-benzofuran-2-yl]methanamine,
(−)-1-[7-(2-fluorophenyl)-2,3-dihydro-1-benzofuran-2-yl]methanamine,
(±)-1-{7-[2-(trifluoromethyl)phenyl]-2,3-dihydro-1-benzofuran-2-yl}methanamine,
(−)-1-{7-[2-(trifluoromethyl)phenyl]-2,3-dihydro-1-benzofuran-2-yl}methanamine,
(+)-1-{7-[2-(trifluoromethyl)phenyl]-2,3-dihydro-1-benzofuran-2-yl}methanamine,
(±)-1-[7-(2,6-dimethylphenyl)-2,3-dihydro-1-benzofuran-2-yl]methanamine,
(−)-1-[7-(2,6-dimethylphenyl)-2,3-dihydro-1-benzofuran-2-yl]methanamine,
(+)-1-[7-(2,6-dimethylphenyl)-2,3-dihydro-1-benzofuran-2-yl]methanamine,
(±)-1-[7-(2-methoxyphenyl)-2,3-dihydro-1-benzofuran-2-yl]methanamine,
(±)-1-[7-(2-chlorophenyl)-2,3-dihydro-1-benzofuran-2-yl]methanamine,
(±)-1-[7-(2,4-dichlorophenyl)-2,3-dihydro-1-benzofuran-2-yl]methanamine,
(±)-1-[5-chloro-7-(2-chlorophenyl)-2,3-dihydro-1-benzofuran-2-yl]methanamine,
(±)-1-[5-chloro-7-(2-methylphenyl)-2,3-dihydro-1-benzofuran-2-yl]methanamine,
(+)-1-[5-chloro-7-(2-methylphenyl)-2,3-dihydro-1-benzofuran-2-yl]methanamine,
(−)-1-[5-chloro-7-(2-methylphenyl)-2,3-dihydro-1-benzofuran-2-yl]methanamine,
(±)-1-[4-fluoro-7-(2-methylphenyl)-2,3-dihydro-1-benzofuran-2-yl]methanamine,
(±)-1-[7-(2-chlorophenyl)-5-fluoro-2,3-dihydro-1-benzofuran-2-yl]methanamine,
(+)-1-[7-(2-chlorophenyl)-5-fluoro-2,3-dihydro-1-benzofuran-2-yl]methanamine,
(−)-1-[7-(2-chlorophenyl)-5-fluoro-2,3-dihydro-1-benzofuran-2-yl]methanamine,
(±)-1-[5-fluoro-7-(2-methylphenyl)-2,3-dihydro-1-benzofuran-2-yl]methanamine,
(+)-1-[5-fluoro-7-(2-methylphenyl)-2,3-dihydro-1-benzofuran-2-yl]methanamine,
(−)-1-[5-fluoro-7-(2-methylphenyl)-2,3-dihydro-1-benzofuran-2-yl]methanamine,
(±)-1-[5-fluoro-7-(2-fluorophenyl)-2,3-dihydro-1-benzofuran-2-yl]methanamine,
(±)-1-{5-fluoro-7-[2-(trifluoromethyl)phenyl]-2,3-dihydro-1-benzofuran-2-yl}methanamine,
(±)-1-[4,5-difluoro-7-(2-methylphenyl)-2,3-dihydro-1-benzofuran-2-yl]methanamine,
(±)-1-(5-chloro-2-methyl-7-phenyl-2,3-dihydro-1-benzofuran-2-yl)methanamine,
(+)-1-[7-(2-methoxyphenyl)-2,3-dihydro-1-benzofuran-2-yl]methanamine,
(−)-1-[7-(2-chlorophenyl)-2,3-dihydro-1-benzofuran-2-yl]methanamine,
(+)-1-[7-(2-chlorophenyl)-2,3-dihydro-1-benzofuran-2-yl]methanamine,
(±)-1-[7-(2,6-difluorophenyl)-2,3-dihydro-1-benzofuran-2-yl]methanamine,
(±)-1-[7-(2,6-dichlorophenyl)-2,3-dihydro-1-benzofuran-2-yl]methanamine,
(−)-1-[7-(2,6-dichlorophenyl)-2,3-dihydro-1-benzofuran-2-yl]methanamine,
(+)-1-[7-(2,6-dichlorophenyl)-2,3-dihydro-1-benzofuran-2-yl]methanamine,
(±)-1-[7-(2,4-dimethoxyphenyl)-2,3-dihydro-1-benzofuran-2-yl]methanamine,
(−)-1-[7-(2,4-dimethoxyphenyl)-2,3-dihydro-1-benzofuran-2-yl]methanamine,
(+)-1-[7-(2,4-dimethoxyphenyl)-2,3-dihydro-1-benzofuran-2-yl]methanamine,
(±)-1-[7-(2,4-difluorophenyl)-2,3-dihydro-1-benzofuran-2-yl]methanamine,
(+)-1-[7-(2,4-difluorophenyl)-2,3-dihydro-1-benzofuran-2-yl]methanamine,
(−)-1-[7-(2,4-difluorophenyl)-2,3-dihydro-1-benzofuran-2-yl]methanamine,
(−)-1-[7-(2,4-dichlorophenyl)-2,3-dihydro-1-benzofuran-2-yl]methanamine, TABLE 1-a-continued Exemplary Compounds of formula I:

(+)-1-[7-(2,4-dichlorophenyl)-2,3-dihydro-1-benzofuran-2-yl]methanamine,
(−)-1-{5-fluoro-7-[2-(trifluoromethyl)phenyl]-2,3-dihydro-1-benzofuran-2-yl}methanamine,
(+)-1-(5-fluoro-7-[2-(trifluoromethyl)phenyl]-2,3-dihydro-1-benzofuran-2-yl}methanamine,
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran--yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}ethanamine,
(±)-{[7-(2,6-dichlorophenyl)-5-fluoro-2,3-dihydro-1-benzofuran-2-yl]methyl}dimethylamine,
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{[5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(5-chloro-2-methoxyphenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine,
(−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(−)-{[5-chloro-7-(2,6-dichlorophenyl)-2,3-dihydro-1-benzofuran-2-yl]methyl}amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-([5-chloro-7-(2,6-dimethylphenyl)-2,3-dihydro-1-benzofuran-2-yl]methyl}ethanamine,
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine, TABLE 1-a-continued Exemplary Compounds of formula I:

(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxylphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-[(N-methyl-1-[7-(2-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine, TABLE 1-a-continued Exemplary Compounds of formula I:

(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-N-methyl-1-[7-(2,3-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-N-methyl-1-[7-(2,4-dimethoxyphenyl)-5-(trifluoromethyl)-2,3-dihydro-1-benzofuran-2-yl]methanamine,
(+){[7-(2,6-dichlorophenyl)-5-fluoro-2,3-dihydro-1-benzofuran-2-yl]methyl}methylamine,
(−){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{2-[6-chloro-7-(2-chlorophenyl)-2,3-dihydro-1-benzofuran-2-yl]ethyl}amine,
(±)-{2-[7-(2,6-dichlorophenyl)-5-fluoro-2,3-dihydro-1-benzofuran-2-yl]ethyl}amine,
(±)-{2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{N-methyl-1-[(7-(2,4,6-trichlorophenyl)-2,3-dihydro-1-benzofuran-2-yl]methanamine,
(−)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;
or a pharmaceutically acceptable salt thereof.

Compounds of formula I for use in accordance with the present invention may be obtained or produced according to any available means including methods described in detail in U.S. patent application Ser. No. 10/970,714, filed Oct. 21, 2004, U.S. provisional patent application Ser. Nos. 60/621,023, filed Oct. 21, 2004, and 60/621,024, filed Oct. 21, 2004, and PCT publication number WP2005/044812, the entirety of each of which is hereby incorporated herein by reference.

2. Antidepressant Agents

In certain embodiments, compounds of the present invention are administered in combination with one or more antidepressive agents. Suitable antidepressant agents include, for example, serotonin reuptake inhibitors (SRIs), norepinephrine reuptake inhibitors (NRIs), combined serotonin-norepinephrine reuptake inhibitors (SNRIs), monoamine oxidase inhibitors (MAOIs), reversible inhibitors of monoamine oxidase (RIMAs), phosphodiesterase-4 (PDE4) inhibitors, corticotropin releasing factor (CRF) antagonists, alpha.-adrenoreceptor antagonists or other compounds including atypical antidepressants. Additional antidepressants for administering in combination with compounds of the present invention include triple uptake inhibitors such as DOV 216303 and DOV 21947 . . . ; melatonin agonists such as agomelotine, super neurotransmitter uptake blockers (SNUBs; e.g., NS-2389 from GlaxoSmithKline and Neurosearch; (R)-DDMA from Sepracor), and/or substance P/neurokinin receptor antagonists (e.g., aprepitant/MK-869 from Merck; NKP-608 from Novartis; CPI-122721 from Pfizer; $R^{673}$ from Roche; TAK637 from Takeda; and GW-97599 from GlaxoSmithKline).

Another class of antidepressant agents that may be used in the present invention are noradrenergic and specific serotonergic antidepressants (NaSSAs), such as mirtazepine (see, for example, U.S. Pat. No. 5,178,878, the entire contents of which are incorporated herein by reference).

Suitable NRIs that may be used in the present invention include tertiary amine tricyclics and secondary amine tricyclics. Suitable examples of tertiary amine tricyclics include: amitriptyline, clomipramine, doxepin, imipramine (See U.S. Pat. No. 2,554,736, incorporated herein by reference in its entirety) and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Another NRI that may be used in the present invention is reboxetine (Edronax™; 2-[.alpha.-(2-ethoxy)phenoxy-benzyl]morpholine, usually administered as the racemate; See U.S. Pat. No. 4,229,449, incorporated herein by reference in its entirety).

Suitable SSRIs that may be used in the present invention include: citalopram (1-[3-(dimethylamino)propyl]-(4-fluorophenyl)-1,3-dihydr-o-5-isobenzofurancarbonitrile; See U.S. Pat. No. 4,136,193; Christensen et al., *Eur. J. Pharmacol.* 41:153, 1977; Dufour et al., *Int. Clin. Psychopharmacol.* 2:225, 1987; Timmerman et al., ibid., 239, each of which is incorporated herein by reference in its entirety); fluoxetine (N-methyl-3-(p-trifluoromethylphenoxy)-3-phenylpropylamine, marketed in the hydrochloride salt form and as the racemic mixture of its two isoforms; see, for example, U.S. Pat. No. 4,314,081; Robertson et al., *J. Med. Chem.* 31:1412, 1988, each of which is incorporated herein by reference); fluoxetine/olanzapine in ///combination; fluvoxamine (5-methoxy-1-[4-(trifluoromethyl)phenyl]-1-pentanone O-(2-aminoethyl)oxime; See U.S. Pat. No. 4,085,225; Claassen et al., *Brit. J. Pharmacol.* 60:505, 1977; De Wilde et al., *J Affective Disord.* 4:249, 1982; Benfield et al., Drugs 32:313, 1986, each of which is incorporated herein by reference in its entirety); paroxetine (trans-(−)-3-[(1,3-benzodioxol-5-yloxy)methyl]-4-(4-fluo-rophenyl)piperidine; See U.S. Pat. No. 3,912,743; U.S. Pat. No. 4,007,196; Lassen, *Eur. J. Pharmacol.* 47:351, 1978; Hassan et al., *Brit. J. Clin. Pharmacol.* 19:705, 1985; Laursen et al., *Acta Psychial. Scand.* 71:249, 1985; Battegay et al., *Neuropsychobiology* 13:31, 1985, each of which is incorporated herein by reference in its entirety); sertraline, (IS-cis)-4-(3,4-dichlorophenyl)-1,2,3,4-tetrahydro-N-methyl-1-naphthylamine hydrochloride; See U.S. Pat. No. 4,536,518, incorporated herein by reference in its entirety); escitalopram (see U.S. Pat. RE34,712); new $5HT_{1A}$ agonists variza, alnespirone, gepirone, sunepitron, MKC242, vilazodone, eptapirone, and ORG12962 from Organon; and pharmaceutically acceptable salts thereof.

Suitable MAOIs that may be used in the present invention include: isocarboxazid, phenelzine, selegiline and tranylcypromine, and pharmaceutically acceptable salts thereof.

Suitable reversible MAOIs that may be used in the present invention include: moclobemide (4-chloro-N-[2-(4-morpholinyl)-ethyl]benzamide; See U.S. Pat. No. 4,210,754, incorporated herein by reference in its entirety), selegiline, and pharmaceutically acceptable salts thereof.

Suitable SNRIs that may be used in the present invention include venlafaxine (see U.S. Pat. No. 4,535,186, incorporated herein by reference in its entirety; see also U.S. Pat. Nos. 5,916,923, 6,274,171, 6,403,120, 6,419,958, 6,444,708, each of which is incorporated herein by reference in its entirety), and pharmaceutically acceptable salts and analogs, including the O-desmethylvenlafaxine succinate salt; milnacipran (N,N-diethyl-2-aminomethyl-1-phenylcyclopropanecarboxamide; see U.S. Pat. No. 4,478,836; Moret et al., *Neuropharmacology* 24:1211-19, 1985, each of which is incorporated herein by reference in its entirety); nefazodone, (available from Bristol Myers Squibb and Dr. Reddy Labs Inc.); duloxetine; and pharmaceutically acceptable salts thereof.

Suitable CRF antagonists that may be used in the present invention include those compounds described in International Patent Specification Nos. WO 94/13643, WO 94/13644, WO 94/13661, WO 94/13676 and WO 94/13677.

Suitable atypical antidepressants that may be used in the present invention include: buproprion (Wellbutrin™; (.+−.)-1-(3-chlorophenyl)-2-[(1,1-dim-ethylethyl)amino]-1-propanone), lithium, nefazodone, trazodone and viloxazine, and pharmaceutically acceptable salts thereof. Another suitable atypical antidepressant is sibutramine.

Particular antidepressants that may be used in the present invention include, but are not limited to, adinazolam, alaproclate, alnespirone, amineptine, amitriptyline, amitriptyline/chlordiazepoxide combination, amoxapine, aprepitant, atipamezole, azamianserin, bazinaprine, befuraline, bifemelane, binodaline, bipenamol, brofaromine, buproprion, caroxazone, cericlamine, cianopramine, cimoxatone, citalopram, clemeprol, clomipramine, clovoxamine, dazepinil, deanol, demexiptiline, desipramine, O-desmethylvenlafaxine, dibenzepin, dothiepin, doxepin, droxidopa, duloxetine, elzasonan, enefexine, eptapirone, escitalopram, estazolam, etoperidone, femoxetine, fengabine, fezolamine, fluotracen, fluoxetine, fluvoxamine, gepirone, idazoxan, imipramine, indalpine, indeloxazine, iprindole, isocarboxazid, levoprotiline, litoxetine, lofepramine, maprotiline, medifoxamine, metapramine, metralindole, mianserin, milnacipran, minaprine, mirtazapine, moclobemide, montirelin, nebracetam, nefopam, nefozodine, nemititide, nialamide, nomifensine, norfluoxetine, nortriptyline, orotirelin, oxaflozane, paroxetine, pheneizine, pinazepam, pirlindone, pizotyline, protryptiline, reboxetine, ritanserin, robalzotan, roliram, selegiline, sercloremine, sertraline, setiptiline, sibutramine, sulbutiamine, sulpiride, sunepitron, teniloxazine, thozalinone, thymoliberin, tianeptine, tiflucarbine, tofenacin, tofisopam, toloxatone, tomoxetine, tranylcypromine, trazodone, trimiprimine, venlafaxine, veralipride, vilazodone, viloxazine, viqualine, zimelidine and zometrapine, and pharmaceutically acceptable salts thereof, and St. John's wort herb, or Hypencuin perforatum, or extracts thereof.

Suitable classes of anti-anxiety agents for administering in combination with compounds of the present invention include $5-HT_{1A}$ agonists or antagonists, especially $5-HT_{1A}$ partial agonists, neurokinin recepter (NK) antagonists (e.g., saredutant and osanetant) and corticotropin releasing factor (CRF) antagonists. Suitable $5-HT_{1A}$ receptor agonists or antagonists that may be used in the present invention include, in particular, the 5-HT$_{1A}$ receptor partial agonists buspirone, flesinoxan, gepirone and ipsapirone, and pharmaceutically acceptable salts thereof. An example of a compound with 5-HT[A receptor antagonist/partial agonist activity is pindolol new 5HT$_{1A}$ agonists variza, alnespirone, gepirone, sunepitron, MKC242, vilazodone, eptapirone, and ORG12962 from Organon; new 5HT$_{1A}$ antagonists such as robalzotan; new 5-HT$_{1B}$ agonists such as elzasonan; new 5HT$_2$ antagonists such as YM-992 (from Yamanouchi Pharmaceuticals) and nemifitide.

Antidepressant agents for use in accordance with the present invention may be obtained or produced according to any available means.

3. Other Agents

Inventive combinations may further include one or more additional pharmaceutically active agents. For example, according to the present invention, the inventive combinations may be administered in conjunction with one or more other agents that is useful in treating depression or other mood disorders. Alternatively or additionally, inventive combinations may be administered with one or more other pharmaceutical agents active in treating any other symptom or medical condition present in the mammal that is related or unrelated to the depression or mood disorder being experienced by the mammal. Examples of such pharmaceutical agents include, for example, anti-angiogenic agents, anti-neoplastic agents, anti-diabetic agents, anti-infective agents, pain-relieving agents, anti-psychotic agents, gastrointestinal agents, etc., or combinations thereof. Other pharmaceutical agents useful in the practice of the present invention include, for example, adjunctive therapies typically used to enhance the effects of an antidepressant. Such adjunctive agents may include, for instance, mood stabilizers (e.g., lithium, valproic acid, carbamazepine, etc.); pindolol, stimulants (e.g., methylphenidate, dextroamphetamine, etc.); or thyroid augmenting agents (e.g., T$_3$); antipsychotics, anti-anxiety agents (e.g., benzodiazepines), and/or agents that relieve sexual dysfunction (e.g., buspirone, which also has anti-anxiety effects; dopaminergic agents such as amantadine, pramipexole, etc.).

A more complete list of pharmaceutically active agents, can be found in the Physicians' Desk Reference, 55 Edition, 2001, published by Medical Economics Co., Inc., Montvale, N.J. Each of these agents may be administered in conjunction with one or more compounds of formula I according to the present invention. For most or all of these agents, recommended effective dosages and regimes are known in the art; many can be found in the above-referenced Physicians' Desk Reference, 55 Edition, 2001, published by Medical Economics Co., Inc., Montvale, N.J.

Particular pharmaceutical agents useful in conjunction with the inventive combinations are those discussed, for example, in United States Patent Application 2003/0092770, United States Patent Application 2004/0029972, United States Patent Application 2004/00220274, United States Patent Application 2005/0054676, or United States Patent Application 2005/0069936, each of which is incorporated herein by reference in its entirety.

4. Pharmaceutical Compositions

While it is possible for the active ingredients of the inventive combination to be administered as raw chemicals, it is often desirable to present them in the context of one or more pharmaceutical formulations. Pharmaceutical formulations according to the present invention comprise a combination according to the invention together with one or more pharmaceutically acceptable carriers or excipients and optionally other therapeutic agents.

The present invention thus provides a pharmaceutical composition comprising one or more 5-HT$_{2C}$ receptor agonists of formula I:

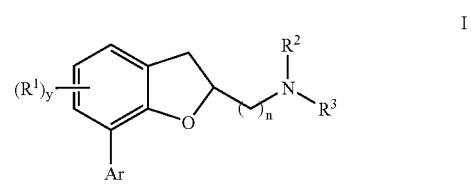

or a pharmaceutically acceptable salt thereof, wherein:

n is one or two;

each of R$^2$ and R$^3$ is independently hydrogen, methyl, ethyl, 2-fluoroethyl, 2,2-difluoroethyl or cyclopropyl;

each R$^1$ is independently hydrogen, halogen, OH, lower alkyl, lower alkoxy, lower haloalkyl, lower haloalkoxy, or CN;

Ar is thienyl, furyl, pyridyl, or phenyl, wherein Ar is optionally substituted with one or more Rx substituents;

each R$^x$ is independently selected from halogen, OH, lower alkyl, lower alkoxy, lower haloalkyl, lower haloalkoxy, or CN; and n is one or two, or pharmaceutically acceptable salts thereof, and one or more antidepressant agents as a combined preparation for simultaneous, separate or sequential administration to treat a patient suffering from or susceptible to depression or other mood disorder.

Agents used in inventive combinations or compositions may be administered simultaneously, in the same or different pharmaceutical formulation, or sequentially. The timing of the sequential administration may desirably be selected to preserve the advantageous effects of the combination and said timing can be determined by a skilled practitioner. In other embodiments, the combinations are combined in a single unit dosage form.

A therapeutically effective amount of the combination will be understood to be an amount which treats, inhibits, prevents or ameliorates one or more symptoms of the depression or mood disorder in question. In certain embodiments of the invention, the combination will show improved efficacy as compared with that achieved by administration of the same amount of either the compound of formula I or the antidepressant agent alone. Furthermore, in certain embodiments, the effective amount of the combination produces fewer side effects than are observed when the antidepressant agent is administered alone at a dose that achieves substantially similar therapeutic efficacy.

The dosages of each of the drugs in the inventive combination may be determined by a physician and will often depend upon the specific circumstances of the depression or mood disorder, as well as the size, age and response pattern of the patient. Dosage guidelines are provided here. For the combination, the dosage guideline for each of the drugs of the combination would be considered.

In general, suitable doses of compound of formula I from about 0.5 mg per day to about 500 mg per day; in some embodiments from about 1 to about 500 mg per day.

A suitable dose of antidepressant agent may be in the range recommended by the manufacturer or reported in the literature. In some embodiments of the invention, the antidepressant agent is used at the low end of the range recommended by the manufacturer, or even below the range, in light of synergistic benefits that can be achieved according to the present invention. The following guidelines are provided for certain antidepressants useful in the practice of the present invention:

Amitryptiline: typically about 100-300 mg/day maintenance dose;

Buproprion: from about 100 to about 300 mg/day;

Citalopram: from about 5 to about 50 mg once/day; preferred, from about 10 to about 30 mg once/day;

Clomipramine: typically about 100-250 mg/day maintenance dose;

Duloxetine: from about 1 to about 30 mg once/day; preferred, from about 5 to about 20 mg once/day;

Fluoxetine: from about 1 to about 80 mg, once/day; preferred, from about 10 to about 40 mg once/day;

Fluvoxamine: from about 20 to about 500 mg once/day; preferred, from about 50 to about 300 mg once/day;

Imipramine: typically about 100-300 mg/day maintenance dose;

Isocarboxazid: typically about 10-20 mg/day maintenance dose;

Maprotiline: typically about 100-200 mg/day maintenance dose;

Mianserin: typically about 30-90 mg/day maintenance dose;

Milnacipran: from about 10 to about 100 mg once-twice/day; preferred, from about 25 to about 50 mg twice/day;

Mirtazapine: typically about 14-45 mg/day maintenance dose;

Moclobemide: typically about 300-600 mg/day maintenance dose;

Nefazodone: typically about 150-300 mg/day maintenance dose;

Nortriptyline: typically about 50-200 mg/day maintenance dose;

Paroxetine: from about 20 to about 50 mg once/day; preferred, from about 20 to about 30 mg once/day;

Phenelzine: typically about 15-60 mg/day maintenance dose;

Reboxetine: from about 1 to about 30 mg, once to four times/day; preferred, from about 5 to about 30 mg once/day;

Sertraline: from about 20 to about 500 mg once/day; preferred, from about 50 to about 200 mg once/day;

Tranylcypromine: typically about 30-60 mg/day maintenance dose;

Trazodone: typically about 75-300 mg/day maintenance dose;

Venlafaxine: from about 10 to about 150 mg once-thrice/day; preferred, from about 25 to about 125 mg thrice/day or about 30 to about 200 mg once a day, for example 37.5 mg, 75 mg, or 150 mg once a day;

Useful carriers for use in inventive pharmaceutical formulations are compatible with the other ingredients in the composition. According to the present invention, compounds of formula I may be administered with antidepressant agents in a single pharmaceutical formulation, or in multiple formulations. Where multiple formulations are employed, each may include both the compound of formula I and the antidepressant agent, or alternatively, each may include only one.

An inventive combination of one or more compounds of formula I and one or more antidepressant agents may conveniently be presented as a pharmaceutical formulation in a unitary dosage form. A convenient unitary dosage formulation contains the active ingredients in amounts from 0.1 mg to 1 g each, for example 1 mg to 500 mg. Typical unit doses may, for example, contain about 0.5 to about 500 mg, or about 1 mg to about 500 mg, of a compound of formula I.

According to the present invention, pharmaceutical formulations may be prepared as "patient packs" containing the whole course of treatment in a single package, for example a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the inventive combination by means of a single patient pack, or patient packs of each formulation, with a package insert directing the patient to the correct use of the invention is a desirable additional feature of this invention.

According to a further aspect of the invention, there is provided a patient pack comprising at least one active ingredient of the combination of the invention and an information insert containing directions on the use of the combination of the invention. In other embodiments, the present invention provides a patient pack comprising both active ingredients of the combination of the invention for simultaneous or sequential administration to a patient, and further comprising an information insert containing directions on the use of the combination of the invention. In certain embodiments, the present invention provides a patient pack comprising both active ingredients of the combination of the invention formulated into a single unit dosage form for administration to a patient, and further comprising an information insert containing directions on the use of the combination of the invention.

According to the present invention, combinations of one or more compounds of formula I and one or more antidepressant agents may be formulated for any mode of delivery including, for example, oral, rectal, nasal, topical (including transdermal, buccal and sublingual), vaginal or parenteral (including subcutaneous, intramuscular, intravenous and intradermal) administration. The formulations may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture). Such methods typically include a step of bringing into association the active ingredient(s) with the carrier which constitutes one or more accessory ingredients. Such accessory ingredients include, for example, fillers, binders, diluents, disintegrants, lubricants, colorants, flavouring agents and wetting agents.

Formulations suitable for oral administration may be presented, for example, as discrete units such as pills, tablets or capsules each containing a predetermined amount of active ingredient; as a powder or granules; as a solution or suspension. The active ingredient(s) may also be present as a bolus or paste, or may be contained within liposomes.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

Formulations suitable for oral administration may alternatively be presented, for example, as liquids. When aqueous suspensions and/or elixirs are desired for oral administration, the active ingredient(s) may be combined with various sweetening or flavoring agents, coloring matter or dyes, and, if so desired, emulsifying and/or suspending agents as well, together with such diluents as water, ethanol, propylene glycol, glycerin and various like combinations thereof. Liquid formulations may be particularly useful for administration to children. In general, when preparing liquid formulations for administration to children, it is desirable to avoid or minimize use of alcohol in the formulation.

Formulations for rectal administration may be presented, for example, as a suppository or enema.

For parenteral administration, solutions of therapeutic agent(s) in either sesame or peanut oil or in aqueous propylene glycol may be employed. Aqueous solutions may be suitably buffered if necessary, and the liquid diluent may be rendered isotonic. Aqueous solutions are suitable for intravenous injection purposes. Oily solutions are suitable for intraarticular, intramuscular and subcutaneous injection purposes. The preparation of all these solutions under sterile conditions is readily accomplished by standard pharmaceutical techniques well known to those skilled in the art. Parenteral formulations may be presented in unit-dose or multi-dose containers, for example, sealed vials and ampoules, and may be stored in a freeze dried (lyophilized) condition requiring only the addition of the sterile liquid carrier, for example, water prior to use.

Preferred compositions for administration of inventive combinations by injection include those comprising the therapeutic agent(s) in association with a surface-active agent (or wetting agent or surfactant) or in the form of an emulsion (as a water-in-oil or oil-in-water emulsion). Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The therapeutic agent(s) may be either dissolved in a pre-mixed emulsion composition or alternatively may be dissolved in an oil (e.g., soybean oil, safflower oil, cottonseed oil, sesame oil, corn oil or almond oil) and an emulsion formed upon mixing with a phospholipid (e.g., eggs phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0.mu.m, particularly 0.1 and 0.5.mu.m, and have a pH in the range of 5.5 to 8.0.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising devise may be attached to a face mask, tent or intermittent positive pressure breathing machine. Solution, suspension, or powder compositions may be administered, preferably orally or nasally, from devices which deliver the formulation in an appropriate manner.

Compositions of the present invention may also be presented for administration in the form of transdermal patches using conventional technology. The compositions may also be administered via the buccal cavity using, for example, absorption wafers.

5. Uses

Administration of the inventive combinations is useful to treat, prevent, delay, or reduce the severity of depression or another mood disorder from which the individual suffers or to which the individual is susceptible, or from one or more symptoms of depression or other mood disorder. For example, according to the present invention, combinations of one or more compounds of formula I and one or more anti-depressive are useful in the treatment of disorders, for example, single episodic or recurrent major depressive disorders, dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder. In some embodiments, inventive combinations are used to treat depression. In some embodiments, inventive combinations are used to treat bipolar disorder.

In other embodiments, compounds of the present invention are useful for treating one or more depressive disorders such as major depressive disorder, seasonal affective disorder, dysthymic disorder, substance-induced mood disorder, depressive disorder not otherwise specified, and treatment resistant depression.

Another aspect of the present invention provides a method for treating one or more mood episodes such as major depressive episode, manic episode, mixed episode, and hypomanic episode; and adjustment disorders such as adjustment disorders with anxiety and/or depressed mood.

Combinations of the present invention are also useful for treating symptoms related to depressive disorders including somatic symptoms such as neuropathic pain and sexual dysfunction. Other somatic symptoms include hopelessness, helplessness, anxiety and worries, memory complaints with or without objective signs of cognitive impairment, loss of feeling of pleasure (anhedonia), slowed movement, irritability, and lack of interest in personal care, such as poor adherence to medical or dietary regimens.

In certain embodiments, the present invention provides a method of treating sexual dysfunction related to depression. In other embodiments, the present invention provides a method of treating sexual dysfunction associated with administering a serotonin reuptake inhibitor (SRI) for treating a depressive or other disorder.

Combinations of the present invention are useful for treating sexual dysfunction in the male (e.g. male erectile dysfunction—MED) and in the female—female sexual dysfunction (FSD), e.g. female sexual arousal disorder (FSAD).

In other embodiments, the present invention provides a method for treating one or more disorders associated with sexual dysfunction including: HSDD, characterized by a deficiency, or absence of, sexual fantasies and desire for sexual activity; FSAD, characterized by a persistent or recurrent inability to attain, or to maintain until completion of the sexual activity, an adequate lubrication-swelling response of sexual excitement; FOD characterized by persistent or recurrent delay in, or absence of, orgasm following a normal sexual excitement phase; Sexual Pain Disorders such as dyspareunia and vaginismus; and/or HSDD characterized by a woman who has no or little desire to be sexual, and has no or few sexual thoughts or fantasies.

It was surprisingly found that compounds of the present invention provide a rapid onset of action as compared with other therapeutic agents typically used for treating depression and depressive disorders.

Alternatively or additionally, inventive combinations may be useful in the treatment of other mood disorders such as dysthymic disorder with early or late onset and with or without atypical features; dementia of the Alzheimer's type, with early or late onset, with depressed mood; vascular dementia with depressed mood, disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

The term "treatment", as used herein, refers to reversing, alleviating, delaying the onset of, inhibiting the progress of, or preventing depression or another mood disorder, or one or more symptoms thereof, as described herein. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

Individuals to be treated in accordance with the present invention include those suffering from depression or a mood disorder, and those susceptible to depression or a mood disorder. In general, a patient is considered to be suffering from depression or a mood disorder if that patient shows an appropriate collection of accepted symptoms. A patient is considered to be susceptible to depression or a mood disorder o if, for example, that patient has a familial history of depression or of the mood disorder, or carries a known genetic susceptibility trait. A patient may also be considered to be susceptible if the patient has shown one or more symptoms of depression, or of the mood disorder, or has experienced an episode of depression or of the mood disorder, in the past.

In some embodiments the inventive cmbinations are useful for treatment-resistant depression. In other embodiments, the inventive combinations, when administered to treat depression or other mood disorders, show fewer undesirable side effects than are observed upon administration of the antidepressant alone in an amount that achieves comparabale relief of depression. Alternatively or additionally, the inventive combinations show more rapid onset of activity than do the antidepressants alone.

Those of ordinary skill in the art will also appreciate that, particularly given the high comorbidity of depression and psychotic disorders, inventive combinations may also be used to treat one or more psychotic disorders, or symptoms thereof. For example, in some embodiments, inventive combinations may be used in the treatment of psychotic disorders or episodes. For example, according to the present invention, combinations of one or more compounds of formula I and one or more anti-psychotic agents may be used in the treatment of schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; dementia, and depression with psychotic features. In some embodiments, inventive combinations are useful in the treatment of bipolar disorder. A more complete description of the aforementioned mental disorders can be found in the Diagnostic and Statistical Manual of Mental Disorders, $4^{th}$ edition, Washington, D.C., American Psychiatric Association (1994), incorporated herein by reference in its entirety. In some embodiments, the inventive combinations are used to treat schizophrenia. In some embodiments, the inventive combinations are used to treat bipolar disorder.

EXAMPLES

Assessment of Effectiveness in Tail Suspension Test

Compound 1, (7-(2,6-dichlorophenyl)-5-fluoro-2,3-dihydrobenzofuran-2-yl)methanamine, was used to exemplify the effectiveness of compounds of the present invention in the tail suspension test. While not a direct model of depression, the tail suspension test is an assay that can evaluate antidepressant-like effects of drugs. Clinically effective drugs such as Prozac (fluoxetine) are effective in this assay. Specifically, they decrease the amount of time the mice spend immobile after being hung upside down by their tails during the test. It is impossible to determine if a mouse is indeed depressed. However, the fact that clinically effective antidepressants reduce immobility lends predictive validity to the model.

Male Swiss Webster mice (Charles River) weighing 20-35 g were used throughout this study. They were housed in groups of five per cage in an AALAC-accredited facility that was maintained on a 12-h light dark cycle (lights on at 0600 h) and had free access to food and water. Experimental groups consisted of 12 mice, randomly assigned to treatment groups. All experiments were performed between 9:00 AM and noon in accordance to the Guide for the Care and Use of Laboratory Animals as adopted and promulgated by the National Institutes of Health (Pub. 85-23, 1985).

Solutions of Compound 1 and paroxetine were freshly prepared. Compound 1 was dissolved in saline and paroxetine was dissolved in distilled water. All drugs were injected i.p. at a volume of 10 ml/kg body weight. Combination treatments were cotreated, 30 minutes prior to the test.

The procedure followed in this study was a variant of the one originally described by Steru et al. (1985). 30 minutes following treatment, the mice were suspended upside down by the tail using adhesive laboratory tape (VWR International), to a flat metal bar connected to a strain gauge within a tail suspension chamber (Med Associates). The time spent immobile during a 6-minute test session was automatically recorded. 8 mice were simultaneously tested within separate chambers. Data collected were expressed as a mean of immobility time and statistical analysis was performed using a one-way ANOVA with least significant difference (LSD) post-hoc test.

Neither Compound 1 (0.1 mg/kg) nor either dose of paroxetine (10 or 30 mg/kg) produced antidepressant-like effects alone. 10 and 30 mg/kg of paroxetine produced 5% and 4% decreases in immobility time respectively when dosed alone. The combination of 10 and 30 mg/kg of paroxetine with 0.1 mg/kg of Compound 1 produced decreases in immobility time of 31% and 23% respectively, indicating an enhancement of the antidepressant-like effects of paroxetine. See FIG. 1.

The entire disclosure of each patent, patent application, and publication cited or described in this document is hereby incorporated by reference.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A composition comprising:
(a) a compound of formula I:

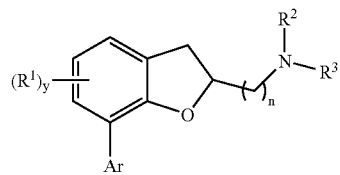

I or a pharmaceutically acceptable salt thereof, wherein:
n is one or two;
each of $R^2$ and $R^3$ is independently hydrogen, methyl, ethyl, 2-fluoroethyl, 2,2-difluoroethyl or cyclopropyl;
each $R^1$ is independently hydrogen, halogen, OH, lower alkyl, lower alkoxy, lower haloalkyl, lower haloalkoxy, or CN;
Ar is thienyl, furyl, pyridyl, or phenyl, wherein Ar is optionally substituted with one or more $R^x$ substituents;
each $R^x$ is independently selected from halogen, OH, lower alkyl, lower alkoxy, lower haloalkyl, lower haloalkoxy, or CN; and
y is 0-3, and
(b) an antidepressant.

2. The composition according to claim 1, wherein one of $R^2$ and $R^3$ is hydrogen and the other $R^2$ and $R^3$ group is hydrogen, methyl, ethyl, 2-fluoroethyl, 2,2-difluoroethyl or cyclopropyl.

3. The composition according to claim 2, wherein both of $R^2$ and $R^3$ are hydrogen.

4. The composition according to claim 1, wherein neither $R^2$ and $R^3$ is hydrogen.

5. The composition according to claim 1, wherein y is zero.

6. The composition according to claim 1, wherein y is other than zero and at least one $R^1$ group is halogen.

7. The composition according to claim 1, wherein y is one and $R^1$ is halogen, OH, lower alkyl, lower alkoxy, trifluoromethyl, trifluoromethoxy, or CN.

8. The composition according to claim 7, wherein y is one and $R^1$ is fluoro or chloro.

9. The composition according to claim 7, wherein said compound is of formula Ia or Ia':

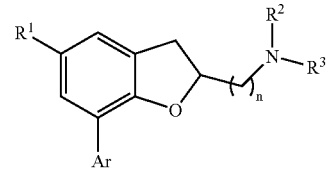

Ia

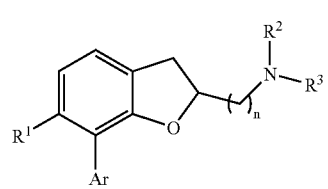

Ia' or a pharmaceutically acceptable salt thereof.

10. The composition according to claim 1, wherein Ar is unsubstituted phenyl.

11. The composition according to claim 1, wherein Ar is phenyl with at least one substituent in the ortho position.

12. The composition according to claim 11, wherein Ar is phenyl with at least one substituent in the ortho position selected from halogen, lower alkyl, lower alkoxy, or trifluoromethyl.

13. The composition according to claim 11, wherein said compound is of formula Ib or Ic:

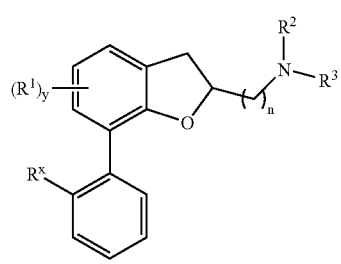

Ib

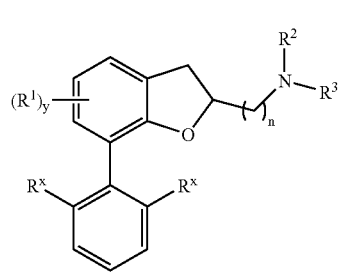

Ic or a pharmaceutically acceptable salt thereof.

14. The composition according to claim 13, wherein said compound is of formula Id, Ie, If, Ig, Ib, or Ii:

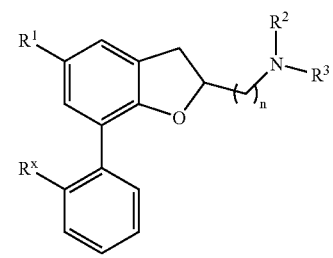

Id

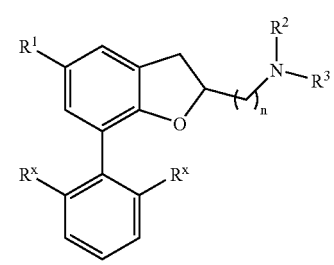

Ie

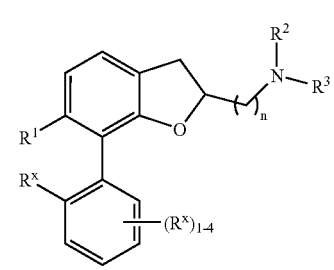

If

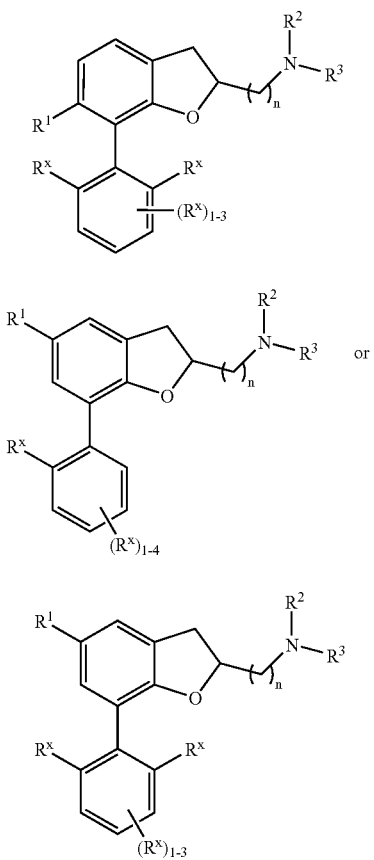
or a pharmaceutically acceptable salt thereof.
15. The composition according to claim 1, wherein Ar is selected from:
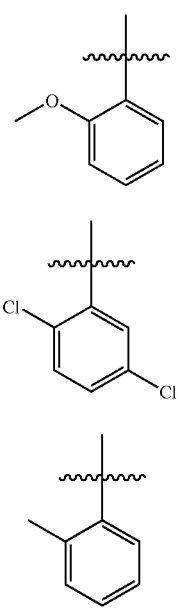
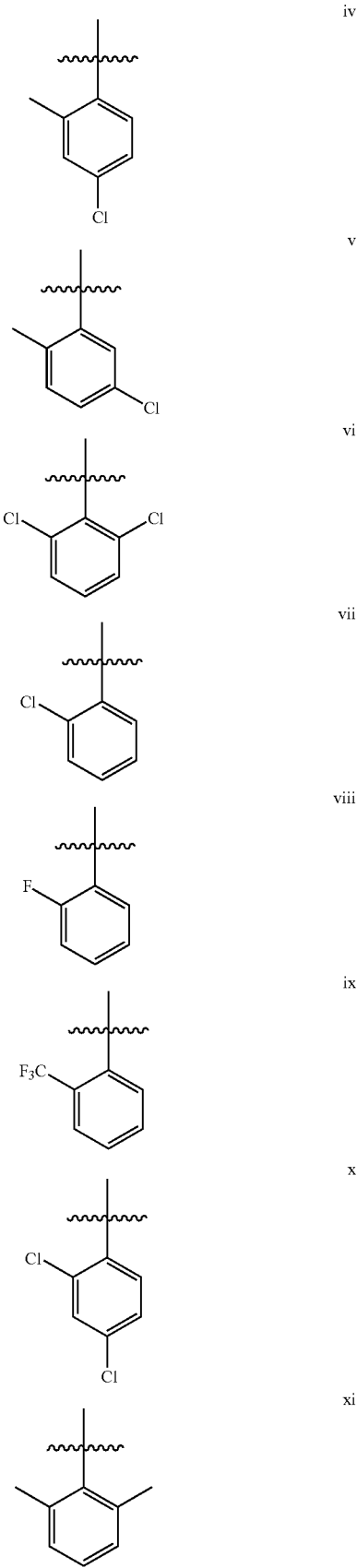

-continued

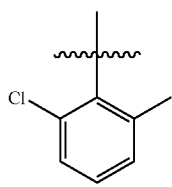
xii

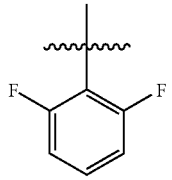
xiii

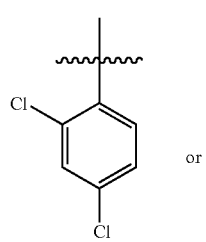
or
xiv

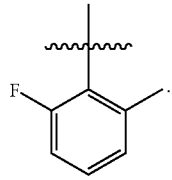
xv

16. The composition according to claim 1, wherein said compound is selected from:
(±)-1-{7-[3,5-bis(trifluoromethyl)phenyl]-2,3-dihydro-1-benzofuran-2-yl}methanamine,
(±)-1-[7-(3-chloro-4-fluorophenyl)-2,3-dihydro-1-benzofuran-2-yl]methanamine,
(±)-1-[7-(3,5-dichlorophenyl)-2,3-dihydro-1-benzofuran-2-yl]methanamine,
(±)-1-(7-phenyl-2,3-dihydro-1-benzofuran-2-yl)methanamine,
(+)-(1-(7-phenyl-2,3-dihydro-1-benzofuran-2-yl)methanamine,
(−)-1-(7-phenyl-2,3-dihydro-1-benzofuran-2-yl)methanamine,
(±)-1-[7-(3-methylphenyl)-2,3-dihydro-1-benzofuran-2-yl]methanamine,
(+)-1-[7-(3-methylphenyl)-2,3-dihydro-1-benzofuran-2-yl]methanamine,
(−)-1-[7-(3-methylphenyl)-2,3-dihydro-1-benzofuran-2-yl]methanamine,
(±)-1-(7-thien-3-yl-2,3-dihydro-1-benzofuran-2-yl)methanamine,
(+)-1-(7-thien-3-yl-2,3-dihydro-1-benzofuran-2-yl)methanamine,
(−)-1-(7-thien-3-yl-2,3-dihydro-1-benzofuran-2-yl)methanamine,
(±)-1-[7-(2-methylphenyl)-2,3-dihydro-1-benzofuran-2-yl]methanamine,
(+)-1-[7-(2-methylphenyl)-2,3-dihydro-1-benzofuran-2-yl]methanamine,
(−)-1-[7-(2-methylphenyl)-2,3-dihydro-1-benzofuran-2-yl]methanamine,
(±)-1-[7-(2-fluorophenyl)-2,3-dihydro-1-benzofuran-2-yl]methanamine,
(+)-1-[7-(2-fluorophenyl)-2,3-dihydro-1-benzofuran-2-yl]methanamine,
(−)-1-[7-(2-fluorophenyl)-2,3-dihydro-1-benzofuran-2-yl]methanamine,
(±)-1-{7-[2-(trifluoromethyl)phenyl]-2,3-dihydro-1-benzofuran-2-yl}methanamine,
(−)-1-{7-[2-(trifluoromethyl)phenyl]-2,3-dihydro-1-benzofuran-2-yl}methanamine,
(+)-1-{7-[2-(trifluoromethyl)phenyl]-2,3-dihydro-1-benzofuran-2-yl}methanamine,
(±)-1-[7-(2,6-dimethylphenyl)-2,3-dihydro-1-benzofuran-2-yl]methanamine,
(−)-1-[7-(2,6-dimethylphenyl)-2,3-dihydro-1-benzofuran-2-yl]methanamine,
(+)-1-[7-(2,6-dimethylphenyl)-2,3-dihydro-1-benzofuran-2-yl]methanamine,
(±)-1-[7-(2-methoxyphenyl)-2,3-dihydro-1-benzofuran-2-yl]methanamine,
(±)-1-[7-(2-chlorophenyl)-2,3-dihydro-1-benzofuran-2-yl]methanamine,
(±)-1-[7-(3-fluorophenyl)-2,3-dihydro-1-benzofuran-2-yl]methanamine,
(±)-1-[7-(3-chlorophenyl)-2,3-dihydro-1-benzofuran-2-yl]methanamine,
(+)-1-[7-(3-chlorophenyl)-2,3-dihydro-1-benzofuran-2-yl]methanamine,
(−)-1-[7-(3-chlorophenyl)-2,3-dihydro-1-benzofuran-2-yl]methanamine,
(±)-1-[7-(3-methoxyphenyl)-2,3-dihydro-1-benzofuran-2-yl]methanamine,
(±)-1-{7-[3-(trifluoromethyl)phenyl]-2,3-dihydro-1-benzofuran-2-yl}methanamine,
(±)-1-[7-(4-methylphenyl)-2,3-dihydro-1-benzofuran-2-yl]methanamine,
(+)-1-[7-(4-methylphenyl)-2,3-dihydro-1-benzofuran-2-yl]methanamine,
(−)-1-[7-(4-methylphenyl)-2,3-dihydro-1-benzofuran-2-yl]methanamine,
(±)-1-[7-(4-fluorophenyl)-2,3-dihydro-1-benzofuran-2-yl]methanamine,
(+)-1-[7-(4-fluorophenyl)-2,3-dihydro-1-benzofuran-2-yl]methanamine,
(−)-1-[7-(4-fluorophenyl)-2,3-dihydro-1-benzofuran-2-yl]methanamine,
(±)-1-[7-(4-chlorophenyl)-2,3-dihydro-1-benzofuran-2-yl]methanamine,
(+)-1-[7-(4-chlorophenyl)-2,3-dihydro-1-benzofuran-2-yl]methanamine,
(−)-1-[7-(4-chlorophenyl)-2,3-dihydro-1-benzofuran-2-yl]methanamine,
(±)-1-[7-(4-methoxyphenyl)-2,3-dihydro-1-benzofuran-2-yl]methanamine,
(+)-1-[7-(4-methoxyphenyl)-2,3-dihydro-1-benzofuran-2-yl]methanamine,
(−)-1-[7-(4-methoxyphenyl)-2,3-dihydro-1-benzofuran-2-yl]methanamine,
(±)-1-{7-[4-(trifluoromethyl)phenyl]-2,3-dihydro-1-benzofuran-2-yl}methanamine,
(±)-1-[7-(2,4-dichlorophenyl)-2,3-dihydro-1-benzofuran-2-yl]methanamine,
(±)-1-(5-chloro-7-phenyl-2,3-dihydro-1-benzofuran-2-yl)methanamine,
(+)-1-(5-chloro-7-phenyl-2,3-dihydro-1-benzofuran-2-yl)methanamine, (−)-1-(5-chloro-7-phenyl-2,3-dihydro-1-benzofuran-2-yl)methanamine,
(±)-1-[5-chloro-7-(2-chlorophenyl)-2,3-dihydro-1-benzofuran-2-yl]methanamine,
(±)-1-[5-chloro-7-(3-methylphenyl)-2,3-dihydro-1-benzofuran-2-yl]methanamine,
(±)-1-[5-chloro-7-(3-chlorophenyl)-2,3-dihydro-1-benzofuran-2-yl]methanamine,
(±)-(5-chloro-7-thien-3-yl-2,3-dihydro-1-benzofuran-2-yl)methylamine,
(−)-(5-chloro-7-thien-3-yl-2,3-dihydro-1-benzofuran-2-yl)methylamine,
(+)-(5-chloro-7-thien-3-yl-2,3-dihydro-1-benzofuran-2-yl)methylamine,
(+)-N-[(5-chloro-7-thien-3-yl-2,3-dihydro-1-benzofuran-2-yl)methyl]-N-methylamine,
(−)-N-[(5-chloro-7-thien-3-yl-2,3-dihydro-1-benzofuran-2-yl)methyl]-N-methylamine,
(±)-1-[5-chloro-7-(2-methylphenyl)-2,3-dihydro-1-benzofuran-2-yl]methanamine,
(+)-1-[5-chloro-7-(2-methylphenyl)-2,3-dihydro-1-benzofuran-2-yl]methanamine,
(−)-1-[5-chloro-7-(2-methylphenyl)-2,3-dihydro-1-benzofuran-2-yl]methanamine,
(±)-1-(4-fluoro-7-phenyl-2,3-dihydro-1-benzofuran-2-yl)methanamine,
(±)-1-[4-fluoro-7-(2-methylphenyl)-2,3-dihydro-1-benzofuran-2-yl]methanamine,
(±)-1-[7-(2-chlorophenyl)-5-fluoro-2,3-dihydro-1-benzofuran-2-yl]methanamine,
(+)-1-[7-(2-chlorophenyl)-5-fluoro-2,3-dihydro-1-benzofuran-2-yl]methanamine,
(−)-1-[7-(2-chlorophenyl)-5-fluoro-2,3-dihydro-1-benzofuran-2-yl]methanamine,
(±)-1-(5-fluoro-7-phenyl-2,3-dihydro-1-benzofuran-2-yl)methanamine,
(±)-1-[5-fluoro-7-(2-methylphenyl)-2,3-dihydro-1-benzofuran-2-yl]methanamine,
(+)-1-[5-fluoro-7-(2-methylphenyl)-2,3-dihydro-1-benzofuran-2-yl]methanamine,
(−)-1-[5-fluoro-7-(2-methylphenyl)-2,3-dihydro-1-benzofuran-2-yl]methanamine,
(±)-1-[5-fluoro-7-(2-fluorophenyl)-2,3-dihydro-1-benzofuran-2-yl]methanamine,
(±)-1-{5-fluoro-7-[2-(trifluoromethyl)phenyl]-2,3-dihydro-1-benzofuran-2-yl}methanamine,
(±)-(4,5-difluoro-7-phenyl-2,3-dihydro-1-benzofuran-2-yl)methylamine,
(±)-1-[4,5-difluoro-7-(2-methylphenyl)-2,3-dihydro-1-benzofuran-2-yl]methanamine,
(±)-1-(5-chloro-2-methyl-7-phenyl-2,3-dihydro-1-benzofuran-2-yl)methanamine,
(±)-(5-chloro-2-methyl-7-thien-3-yl-2,3-dihydro-1-benzofuran-2-yl)methylamine,
(±)-(5-chloro-2-methyl-7-thien-2-yl-2,3-dihydro-1-benzofuran-2-yl)methylamine,
(+)-1-[7-(2-methoxyphenyl)-2,3-dihydro-1-benzofuran-2-yl]methanamine,
(−)-1-[7-(2-chlorophenyl)-2,3-dihydro-1-benzofuran-2-yl]methanamine,
(+)-1-[7-(2-chlorophenyl)-2,3-dihydro-1-benzofuran-2-yl]methanamine,
(+)-1-[7-(3-fluorophenyl)-2,3-dihydro-1-benzofuran-2-yl]methanamine,
(−)-1-[7-(3-fluorophenyl)-2,3-dihydro-1-benzofuran-2-yl]methanamine,
(+)-1-[7-(3-methoxyphenyl)-2,3-dihydro-1-benzofuran-2-yl]methanamine,
(−)-1-[7-(3-methoxyphenyl)-2,3-dihydro-1-benzofuran-2-yl]methanamine,
(−)-1-{7-[3-(trifluoromethyl)phenyl]-2,3-dihydro-1-benzofuran-2-yl}methanamine,
(+)-1-{7-[3-(trifluoromethyl)phenyl]-2,3-dihydro-1-benzofuran-2-yl}methanamine,
(+)-1-{7-[4-(trifluoromethyl)phenyl]-2,3-dihydro-1-benzofuran-2-yl}methanamine,
(−)-1-{7-[4-(trifluoromethyl)phenyl]-2,3-dihydro-1-benzofuran-2-yl}methanamine,
(±)-1-[7-(2,6-difluorophenyl)-2,3-dihydro-1-benzofuran-2-yl]methanamine,
(±)-1-[7-(2,6-dichlorophenyl)-2,3-dihydro-1-benzofuran-2-yl]methanamine,
(−)-1-[7-(2,6-dichlorophenyl)-2,3-dihydro-1-benzofuran-2-yl]methanamine,
(+)-1-[7-(2,6-dichlorophenyl)-2,3-dihydro-1-benzofuran-2-yl]methanamine,
(±)-1-[7-(2,4-dimethoxyphenyl)-2,3-dihydro-1-benzofuran-2-yl]methanamine,
(−)-1-[7-(2,4-dimethoxyphenyl)-2,3-dihydro-1-benzofuran-2-yl]methanamine,
(+)-1-[7-(2,4-dimethoxyphenyl)-2,3-dihydro-1-benzofuran-2-yl]methanamine,
(±)-1-[7-(2,4-difluorophenyl)-2,3-dihydro-1-benzofuran-2-yl]methanamine,
(+)-1-[7-(2,4-difluorophenyl)-2,3-dihydro-1-benzofuran-2-yl]methanamine,
(−)-1-[7-(2,4-difluorophenyl)-2,3-dihydro-1-benzofuran-2-yl]methanamine,
(−)-1-[7-(2,4-dichlorophenyl)-2,3-dihydro-1-benzofuran-2-yl]methanamine,
(+)-1-[7-(2,4-dichlorophenyl)-2,3-dihydro-1-benzofuran-2-yl]methanamine,
(−)-1-{5-fluoro-7-[2-(trifluoromethyl)phenyl]-2,3-dihydro-1-benzofuran-2-yl}methanamine,
(+)-1-{5-fluoro-7-[2-(trifluoromethyl)phenyl]-2,3-dihydro-1-benzofuran-2-yl}methanamine,
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine, (±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(−)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[5-fluoro-7-(3-fluorophenyl)-2,3-dihydro-1-benzofuran-2-yl]methyl}amine,
(±)-{[5-fluoro-7-(3-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine,
(±)-{[5-fluoro-7-(4-chlorophenyl)-2,3-dihydro-1-benzofuran-2-yl]methyl}amine,
(±)-{[5-fluoro-7-(4-methylphenyl)-2,3-dihydro-1-benzofuran-2-yl]methyl}amine,
(±)-{[5-fluoro-7-(4-methoxyphenyl)-2,3-dihydro-1-benzofuran-2-yl]methyl}amine,
(±)-[(5-fluoro-7-thien-3-yl-2,3-dihydro-1-benzofuran-2-yl)methyl]amine,
(±)-{[5-fluoro-7-(3-furyl)-2,3-dihydro-1-benzofuran-2-yl]methyl}amine,
(±)-[(5-fluoro-7-pyridin-2-yl-2,3-dihydro-1-benzofuran-2-yl)methyl]amine,
(±)-[(5-fluoro-7-pyridin-3-yl-2,3-dihydro-1-benzofuran-2-yl)methyl]amine,
(−)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-[(5-fluoro-7-pyridin-4-yl-2,3-dihydro-1-benzofuran-2-yl)methyl]amine,
(±)-[(5-fluoro-7-pyrimidin-5-yl-2,3-dihydro-1-benzofuran-2-yl)methyl]amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(+)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}ethanamine,
(±)-{[7-(2,6-dichlorophenyl)-5-fluoro-2,3-dihydro-1-benzofuran-2-yl]methyl}dimethylamine,
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(3-furyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{((5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(5-chloro-2-methoxyphenyl)-2,3-dihydro-1-benzofuran-2-yl]methyl}amine,
(±)-{[5-chloro-7-(3,4-difluorophenyl)-2,3-dihydro-1-benzofuran-2-yl]methyl}amine,
(±)-{[5-chloro-7-(3-chloro-4-fluorophenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine, (−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(+)-{[5-chloro-7-(2,6-dichlorophenyl)-2,3-dihydro-1-benzofuran-2-yl]methyl}amine,
(−)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-{[5-chloro-7-(2,6-dimethylphenyl)-2,3-dihydro-1-benzofuran-2-yl]methyl}ethanamine,
(±)-{[(5-methyl-7-phenyl-2,3-dihydro-1-benzofuran-2-yl)methyl]amine,
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±) {[5-(trifluoromethyl)-7-(3-methylphenyl)-2,3-dihydro-1-benzofuran-2-yl]methyl}amine,
(±)-{[5-(trifluoromethyl)-7-(3-fluorophenyl)-2,3-dihydro-1-benzofuran-2-yl]methyl}amine,
(±)-{[5-(trifluoromethyl)-7-(3-chlorophenyl)-2,3-dihydro-1-benzofuran-2-yl]methyl}amine,
(±)-{[5-(trifluoromethyl)-7-(3-methoxyphenyl)-2,3-dihydro-1-benzofuran-2-yl]methyl}amine,
(±)-{[5-(trifluoromethyl)-7-(3-(trifluoromethyl)phenyl)-2,3-dihydro-1-benzofuran-2-yl]methyl}amine,
(±)-{[5-(trifluoromethyl)-7-(4-methylphenyl)-2,3-dihydro-1-benzofuran-2-yl]methyl}amine,
(±)-{[5-(trifluoromethyl)-7-(4-fluorophenyl)-2,3-dihydro-1-benzofuran-2-yl]methyl}amine,
(±)-{[5-(trifluoromethyl)-7-(4-chlorophenyl)-2,3-dihydro-1-benzofuran-2-yl]methyl}amine,
(±)-{[5-(trifluoromethyl)-7-(4-methoxyphenyl)-2,3-dihydro-1-benzofuran-2-yl]methyl}amine,
(±)-{[5-(trifluoromethyl)-7-(4-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(3,4-difluorophenyl)-5-(trifluoromethyl)-2,3-dihydro-1-benzofuran-2-yl]methyl}amine,
(±)-{[7-(3-chloro-4-fluorophenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-4-[2-(aminomethyl)-5-(trifluoromethyl)-2,3-dihydro-1-benzofuran-7-yl]benzonitrile
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine, (±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[5-methoxy-7-(3-thienyl)-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxylphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl 1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine, (±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[5-chloro-7-(3,4-difluorophenyl)-2,3-dihydro-1-benzofuran-2-yl]methyl}methylamine,
(±)-[5-chloro-7-(3-chloro-4-fluorophenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-N-methyl-1-[7-(2,3-difluorophenyl)-5-(trifluoromethyl)-2,3-dihydro-1-benzofuran-2-yl]methanamine,
(±)-N-methyl-1-[7-(3,4-difluorophenyl)-5-(trifluoromethyl)-2,3-dihydro-1-benzofuran-2-yl]methanamine,
(±)-N-methyl-1-[7-(2,5-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-{[7-(3-chloro-4-fluorophenyl)-5-(trifluoromethyl)-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine,
(+){[7-(2,6-dichlorophenyl)-5-fluoro-2,3-dihydro-1-benzofuran-2-yl]methyl}methylamine,
(−3){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{2-[6-chloro-7-(2-chlorophenyl)-2,3-dihydro-1-benzofuran-2-yl]ethyl}amine,
(±)-{2-[7-(2,6-dichlorophenyl)-5-fluoro-2,3-dihydro-1-benzofuran-2-yl]ethyl}amine,
(±)-{2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{N-methyl-1-[(7-(2,4,6-trichlorophenyl)-2,3-dihydro-1-benzofuran-2-yl]methanamine,
(−)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine, (+)-{[5-chloro-7-(2,5-dichlorophenyl)-2,3-dihydro-1-benzofuran-2-yl]methyl}methylamine, (−)-{[5-chloro-7-(2,5-dichlorophenyl)-2,3-dihydro-1-benzofuran-2-yl]methyl}methylamine, (−)-{[5-chloro-7-(2,6-dimethylphenyl)-2,3-dihydro-1-benzofuran-2-yl]methyl}methylamine, (+)-{[5-chloro-7-(2,6-dimethylphenyl)-2,3-dihydro-1-benzofuran-2-yl]methyl}methylamine, (+)-{[7-(2,3-dimethoxyphenyl)-5-methyl-2,3-dihydro-1-benzofuran-2-yl]methyl}methylamine, (−)-{[7-(2,3-dimethoxyphenyl)-5-methyl-2,3-dihydro-1-benzofuran-2-yl]methyl}methylamine, (−)-{[7-(2,3-dimethoxyphenyl)-5-fluoro-2,3-dihydro-1-benzofuran-2-yl]methyl}methylamine, or (+)-{[7-(2,3-dimethoxyphenyl)-5-fluoro-2,3-dihydro-1-benzofuran-2-yl]methyl}methylamine;

or a pharmaceutically acceptable salt thereof.

* * * * *